United States Patent
Wakana et al.

(10) Patent No.: US 11,371,950 B2
(45) Date of Patent: Jun. 28, 2022

(54) MOISTURE DETECTION ELEMENT, EXHALED GAS DETECTOR, EXHALATION TEST SYSTEM, AND MANUFACTURING METHOD OF EXHALATION DETECTION ELEMENT

(71) Applicant: HITACHI, LTD., Tokyo (JP)

(72) Inventors: Hironori Wakana, Tokyo (JP); Masuyoshi Yamada, Tokyo (JP)

(73) Assignee: HITACHI, LTD., Tokyo (JP)

( * ) Notice: Subject to any disclaimer, the term of this patent is extended or adjusted under 35 U.S.C. 154(b) by 220 days.

(21) Appl. No.: 16/824,531

(22) Filed: Mar. 19, 2020

(65) Prior Publication Data

US 2020/0300797 A1     Sep. 24, 2020

(30) Foreign Application Priority Data

Mar. 22, 2019   (JP) .............................. JP2019-054768

(51) Int. Cl.
   *G01N 27/12* (2006.01)
   *G01N 33/497* (2006.01)

(52) U.S. Cl.
   CPC ......... *G01N 27/121* (2013.01); *G01N 27/123* (2013.01); *G01N 33/4972* (2013.01)

(58) Field of Classification Search
   CPC ............... G01N 27/121; G01N 27/123; G01N 33/4972; G01N 27/223
   See application file for complete search history.

(56) References Cited

U.S. PATENT DOCUMENTS

| | | | |
|---|---|---|---|
| 3,715,702 A * | 2/1973 | Nicholas ................ | H01H 35/42 340/602 |
| 4,898,476 A | 2/1990 | Herrmann et al. | |
| 4,970,122 A | 11/1990 | Palanisamy | |
| 5,767,687 A * | 6/1998 | Geist .................... | G01N 27/221 324/686 |

(Continued)

FOREIGN PATENT DOCUMENTS

| | | |
|---|---|---|
| JP | 62-182642 A | 8/1987 |
| JP | 2011-053049 A | 3/2011 |

(Continued)

OTHER PUBLICATIONS

Japanese Office Action dated Mar. 8, 2022 for Japanese Patent Application No. 2019-054768.

(Continued)

*Primary Examiner* — David J Bolduc
(74) *Attorney, Agent, or Firm* — Volpe Koenig

(57) ABSTRACT

A moisture detection element includes: an insulating substrate of an insulating material; an application part which is formed on the insulating substrate and to which a voltage is applied; an output part which is formed on the insulating substrate and configured to output a voltage signal corresponding in response to a current flowing through an electric path via water molecules adhering to a surface of the insulating substrate under the voltage applied to the application part; and a conductive film which is electrically insulated from the application part and the output part and is provided on the insulating substrate. An insulating film of an insulating material is provided on the application part, the output part, and the conductive film.

16 Claims, 24 Drawing Sheets

(56) References Cited

U.S. PATENT DOCUMENTS

| | | | | |
|---|---|---|---|---|
| 6,126,311 | A * | 10/2000 | Schuh | G01N 25/68 374/21 |
| 6,742,387 | B2 * | 6/2004 | Hamamoto | G01N 19/10 73/335.04 |
| 7,834,646 | B2 * | 11/2010 | Chambon | G01N 27/22 324/686 |
| 8,773,271 | B1 * | 7/2014 | Stevens | G01N 27/048 340/604 |
| 9,164,052 | B1 * | 10/2015 | Speer | G01N 27/22 |
| 2004/0182153 | A1 * | 9/2004 | Hamamoto | G01N 27/225 73/335.04 |
| 2006/0032761 | A1 * | 2/2006 | Oguri | G01N 27/121 204/421 |
| 2006/0144438 | A1 * | 7/2006 | Dresselhaus | F16K 37/0091 200/61.04 |
| 2006/0186901 | A1 * | 8/2006 | Itakura | G01N 27/223 324/689 |
| 2009/0090577 | A1 * | 4/2009 | Takahashi | G01N 33/4972 340/576 |
| 2010/0063409 | A1 * | 3/2010 | Hok | A61B 5/0836 600/532 |
| 2010/0307238 | A1 * | 12/2010 | Van Popta | G01N 27/225 73/335.04 |
| 2011/0259099 | A1 * | 10/2011 | Hong | G01N 27/223 29/874 |
| 2013/0207673 | A1 * | 8/2013 | Tondokoro | G01N 27/223 29/592 |
| 2013/0344609 | A1 * | 12/2013 | Mayer | G01N 33/0032 422/98 |
| 2014/0026642 | A1 * | 1/2014 | O'Connell | G01N 27/223 73/31.05 |
| 2014/0167791 | A1 * | 6/2014 | Feyh | G01N 27/121 438/49 |
| 2015/0177196 | A1 * | 6/2015 | Sussner | G01N 29/2406 73/24.04 |
| 2016/0223490 | A1 * | 8/2016 | Astley | G01N 27/4071 |
| 2017/0167995 | A1 * | 6/2017 | Kawakita | G01N 27/223 |
| 2018/0074081 | A1 * | 3/2018 | Wakana | H04N 5/23206 |
| 2018/0284048 | A1 * | 10/2018 | Wakana | G01N 33/0037 |
| 2019/0162715 | A1 * | 5/2019 | Wakana | G01N 33/4972 |
| 2019/0257779 | A1 * | 8/2019 | Nakane | G01N 27/223 |
| 2020/0158674 | A1 * | 5/2020 | Nakane | H01L 27/0274 |
| 2020/0158675 | A1 * | 5/2020 | Inoue | G01N 27/226 |
| 2020/0158676 | A1 * | 5/2020 | Inoue | G01N 27/226 |
| 2020/0158677 | A1 * | 5/2020 | Nakane | G01N 27/223 |
| 2020/0249185 | A1 * | 8/2020 | Kawakita | G01N 27/048 |

FOREIGN PATENT DOCUMENTS

| | | |
|---|---|---|
| JP | 2018-136134 A | 8/2018 |
| SU | 898312 A1 | 1/1982 |

OTHER PUBLICATIONS

European Office Action and Search Report dated Aug. 3, 2020 for European Patent Application No. 20162753.6.

* cited by examiner

FIG. 4
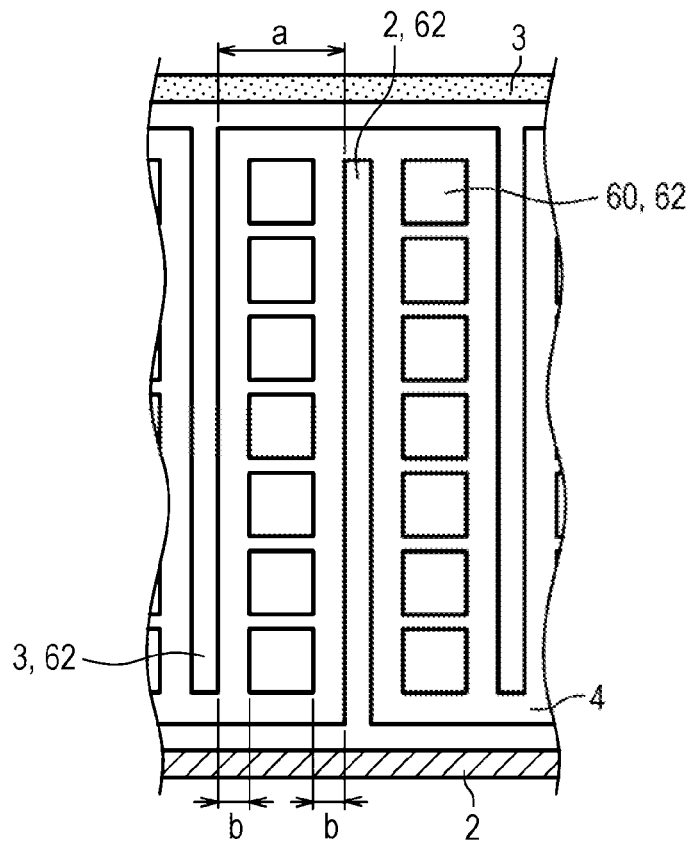
FIG. 5
| INTERELECTRODE DISTANCE ($\mu m$) | OUTPUT VOLTAGE vo | |
|---|---|---|
| | WITHOUT AUXILIARY ELECTRODE | WITH AUXILIARY ELECTRODE |
| 20 | 2.2V | 2.8V (b=5$\mu m$) |
| 15 | 2.5V | — |
| 10 | 2.8V | — |
FIG. 6
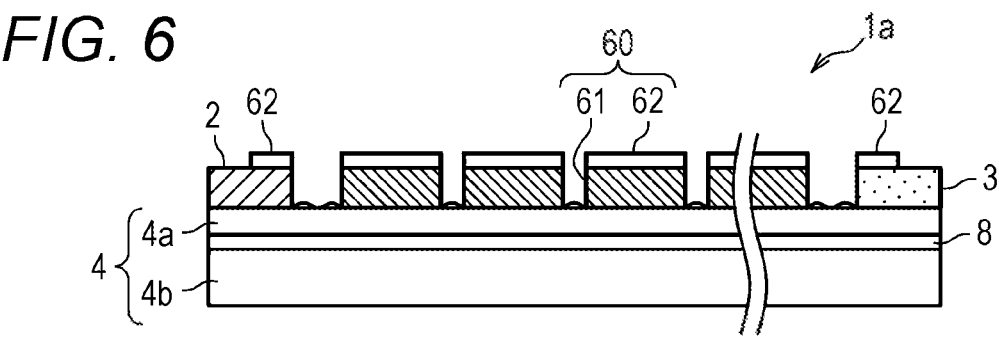

MOISTURE DETECTION ELEMENT, EXHALED GAS DETECTOR, EXHALATION TEST SYSTEM, AND MANUFACTURING METHOD OF EXHALATION DETECTION ELEMENT

CROSS REFERENCE TO RELATED APPLICATIONS

This application claims the foreign priority benefit 35 U.S.C. § 119 of Japanese patent application No. 2019-054768 filed on Mar. 22, 2019, the disclosure of which is incorporated herein by reference.

BACKGROUND OF THE INVENTION

1. Field of the Invention

The present invention relates to a technique of a moisture detection element, an exhaled gas detector, and an exhalation test system used for measuring exhalation, and a manufacturing method of the exhalation detection element.

2. Description of the Related Art

In the future automatic driving of automobiles, when switching between automatic driving and manual driving, it is necessary to detect whether a driver is drunk and detect human conditions or the like.

Conventional alcohol detectors measure the concentration of alcohol contained in the exhalation by introducing the exhalation of the subject. This alcohol detector does not have a function of recognizing human exhalation, and thus, in exhalation, there is a possibility that unauthorized use or the like may occur by blowing outside air or the like instead of own exhalation.

In order to prevent such unauthorized use, it is necessary to test whether the air introduced into the alcohol detector is exhalation. Since human exhalation is saturated with water vapor unlike outside air, the amount of water vapor in the air introduced into the alcohol detector is measured. That is, by measuring the moisture, it can be determined whether or not the introduced air is human exhalation, and unauthorized use can be prevented.

In addition, in the practical application of such a technique, it is important to ensure robustness with respect to the environment of the device, and measures such as a reduction in failure rate are required.

In a conventional alcohol detector, in order to determine whether or not the introduced air is a human exhalation, the flow rate of the introduced outside air is measured, or oxygen gas is detected.

For example, an alcohol detector described in JP 2011-53049 A is disclosed. In JP 2011-53049 A, "in the an alcohol detector 101 composed of a composite gas sensor, the fan 6 is arranged on the upstream side of the device main body 7, and the temperature sensor 9, the humidity sensor 11, the alcohol detection sensor 12, and the oxygen sensor 13 is arranged in this order on the downstream side of the fan 6, so that the influence of heat generated by the alcohol detection sensor 12 and the oxygen sensor 13 does not affect the temperature sensor 9 and the humidity sensor 11" (see summary).

SUMMARY OF THE INVENTION

Here, the humidity sensor provided in the alcohol detector described in JP 2011-53049 A is installed for the purpose of constantly monitoring the change in the amount of moisture in the air, which is considered to affect the alcohol sensor. In addition, as the humidity sensor provided in the alcohol detector described in JP 2011-53049 A, a capacitance change type humidity sensor (which is configured to measure the conductivity and capacitance change of the sensor element) is used. Therefore, the alcohol detector described in JP 2011-53049 A is not installed for the purpose of determining whether or not human exhalation has been introduced by detecting saturated water vapor.

The alcohol detector described in JP 2011-53049 A includes a fan, and thus, the alcohol detector cannot be reduced in size and is not suitable for mobile use. In addition, the alcohol detector described in JP 2011-53049 A does not detect saturated water vapor, and thus, it is insufficient to detect whether or not the introduced outside air is human exhalation.

When the alcohol detector is to be made portable by reducing the size and the power consumption, a fine pattern electrode is used, and thus a sensor error occurs due to dust in the atmosphere.

The present invention has been made in view of such a background, and an object of the present invention is to improve a robustness of a moisture detection element that realizes an exhalation recognition function.

In order to solve the above-described problems, the present invention includes: an insulating substrate of an insulating material; an application part which is formed on the insulating substrate and to which a voltage is applied; and an output part which is formed on the insulating substrate and configured to output a voltage signal in response to a current flowing through an electric path via water molecules adhering to a surface of the insulating substrate under the voltage applied to the application part. An insulation of an insulating material is provided on the application part and the output part.

Other solutions will be described as appropriate in the embodiments.

According to the present invention, the robustness of the moisture detection element which realizes the exhalation recognition function can be improved.

BRIEF DESCRIPTION OF THE DRAWINGS

FIG. 4 is an enlarged view of a part of the moisture detection element;

FIG. 5 is a table showing the relationship between the interelectrode distance and the output voltage vo;

FIG. 6 is a view illustrating an example of a moisture detection element provided with a heater;

FIG. 20 is a view illustrating an example (Example 1) of a mobile type exhalation test device 700a;

DESCRIPTION OF THE PREFERRED EMBODIMENTS

Next, modes for carrying out the present invention (referred to as "embodiments") will be described in detail with reference to the drawings as appropriate. Incidentally, in each drawing, exaggeration, deformation, and the like are made, and the dimensions of each part do not necessarily match among the drawings.

[Moisture Detection Element 1]

(Structure of Moisture Detection Element 1)

Figure 1:
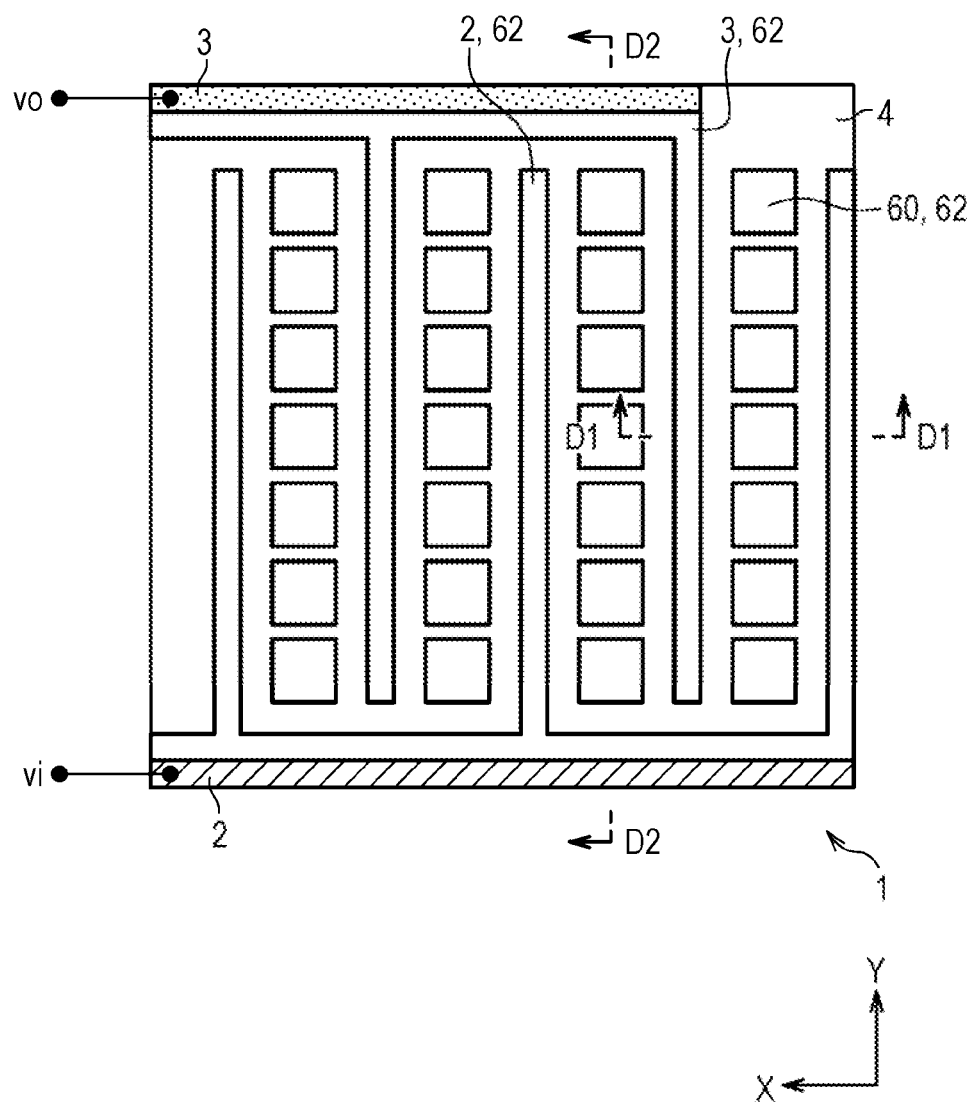
FIG. 1 is a view illustrating a structure of a moisture detection element according to this embodiment.
Figure 2A:
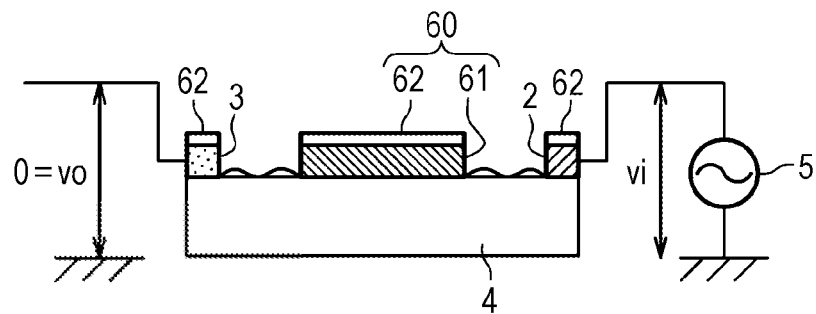
FIG. 2A is a view for explaining a principle (before moisture adhesion) that the moisture detection element according to this embodiment detects moisture.
Figure 2B:
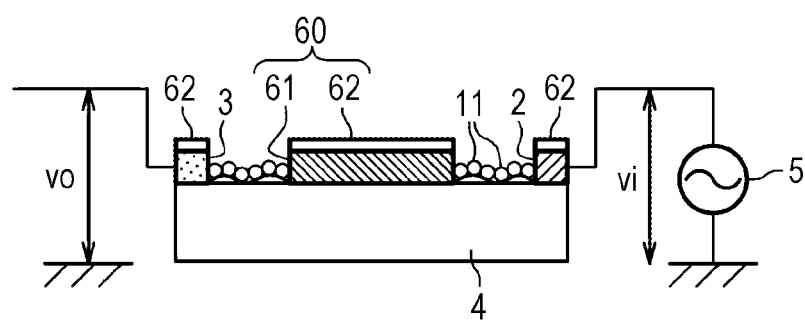
FIG. 2B is a view for explaining a principle (after moisture adhesion) that the moisture detection element according to this embodiment detects moisture.
Figure 2C:
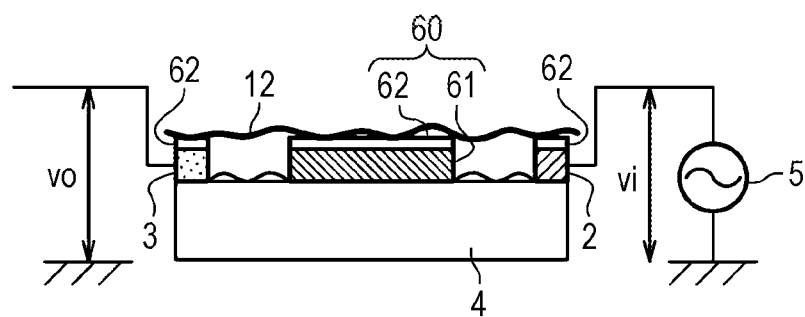
FIG. 2C is a schematic cross-sectional view illustrating the state of the moisture detection element to which dust adheres.
Figure 2D:
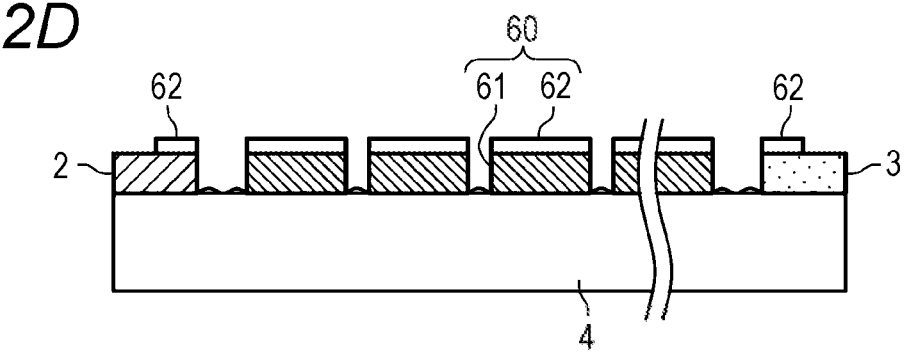
FIG. 2D is a schematic cross-sectional view taken along line D2-D2 of FIG. 1.

FIG. 1 is a view illustrating a structure of a moisture detection element 1 according to this embodiment. FIGS. 2A and 2B are views for explaining a principle that the moisture detection element 1 according to this embodiment detects moisture. FIG. 2A is a schematic cross-sectional view illustrating the principle of the moisture detection element 1 before moisture adhesion, and FIG. 2B is a schematic sectional view illustrating the principle of the moisture detection element 1 after moisture adhesion. In addition, FIG. 2C is a schematic cross-sectional view illustrating the state of the moisture detection element 1 to which dust 12 adheres. Incidentally, FIGS. 2A to 2C are schematic cross-sectional views taken along line D1-D1 of FIG. 1. FIG. 2D is a schematic cross-sectional view taken along line D2-D2 of FIG. 1.

As illustrated in FIG. 1, the moisture detection element (moisture detection part) 1 is connected to a power supply 5 (see FIGS. 2A and 2B) and includes an application electrode (application part) 2, a detection electrode (output part) 3, an auxiliary electrode 60, and an insulating substrate 4.

The application electrode 2 is an electrode to which an AC voltage vi is applied by the power supply 5.

The detection electrode 3 is an electrode that detects an (alternating current) output voltage (voltage signal) vo when moisture is detected.

The insulating substrate 4 is configured by a hydrophilic insulating substrate. Specifically, at least the surface is configured by an oxide such as an insulating metal oxide. Incidentally, the shape of the insulating substrate 4 may not be a substrate shape.

Incidentally, as illustrated in FIG. 1, the application electrode 2 and the detection electrode 3 have a comb shape. The application electrode 2 and the detection electrode 3 are installed separately on the insulating substrate 4 so as to be opposed to each other so that their comb teeth are engaged with each other. In this way, the area of a moisture adhesion part (reaction portion) can be enlarged, and a sensitivity can be improved.

As illustrated in FIGS. 1 and 2A, the auxiliary electrode 60 is installed between the application electrode 2 and the detection electrode 3. In FIGS. 2A and 2D, the auxiliary electrode 60 is installed on the insulating substrate 4 and is configured by a conductive film 61 which is a conductive film and an insulating film (insulation) 62 which is arranged on the conductive film 61 and is an insulating film. As illustrated in FIGS. 2A and 2D, the insulating film 62 is formed only on the upper surface of the conductive film 61 and is not formed on the side surface of the conductive film 61.

Here, the conductive film 61 is not electrically connected to the application electrode 2 or the detection electrode 3. That is, the conductive film 61 is electrically insulated (independent) from the application electrode 2 and the detection electrode 3. Further, as illustrated in FIGS. 1, 2A, and 2D, the insulating film 62 is also arranged on part of the application electrode 2 and the detection electrode 3. Here, as illustrated in FIGS. 2A and 2D, the insulating film 62 is formed only on the upper surfaces of the application electrode 2 and the detection electrode 3 and is not formed on side surfaces of the application electrode 2 and the detection electrode 3.

In the application electrode 2 and the detection electrode 3, the place where the insulating film 62 is arranged is a place where a short circuit may occur due to the adhesion of the dust 12. In this way, the amount of the insulating film 62 can be reduced, and the cost can be reduced.

Incidentally, the insulating film 62 is configured by a metal oxide film, polyimide, resin, or the like.

For example, the capacitance humidity sensor described in JP 2011-53049 A is intended to measure humidity in the air.

On the other hand, the moisture detection element 1 according to this embodiment is intended for detection of exhalation at a high humidity (substantially saturated state). Therefore, the moisture detection element 1 of this embodiment is not intended to measure the amount of moisture in the air, but only needs to be able to detect high humidity air (exhalation).

(Moisture Detection Principle)

Next, the principle of moisture detection of the moisture detection element 1 in this embodiment will be described with reference to FIGS. 2A and 2B.

As illustrated in FIG. 2A, no electric current is applied between the detection electrode 3 and the application electrode 2 before moisture adhesion. Therefore, although the AC voltage vi is applied to the application electrode 2, no voltage is detected from the detection electrode 3 (vo=0).

Then, as illustrated in FIG. 2B, when water molecules 11 sufficiently adheres to the insulating substrate 4 of the moisture detection element 1, the detection electrode 3 and the application electrode 2 are energized with the water molecules 11 and the conductive film 61 as a path. Then, the AC voltage vi applied from the detection electrode 3 to the application electrode 2 is detected (output). The moisture detection element 1 detects moisture on the basis of the detected (output) voltage (output voltage vo). The output voltage vo is an AC voltage.

As described above, when the water molecules 11 included in the exhalation adhere to the insulating substrate 4, energization is performed using the water molecules 11 and the conductive film 61 as a path. Accordingly, the output voltage vo is detected by the detection electrode 3. Therefore, the moisture detection element 1 according to this embodiment only needs to have the insulating substrate 4 that is wide enough to allow the water molecules 11 to adhere thereto, and can be reduced in size.

The output voltage vo is almost 0 before moisture (water molecule 11) adheres to the insulating substrate 4, whereas the output voltage vo is almost the same as the AC voltage vi (theoretically) after the adhesion of moisture (water molecule 11). Accordingly, an excellent signal/noise (S/N) ratio can be realized.

Incidentally, the surface of the insulating substrate 4 has an uneven structure as illustrated in FIGS. 2A and 2B. As described above, the surface of the insulating substrate 4 has unevenness, and thus the surface area of the insulating substrate 4 can be increased. That is, since the surface of the insulating substrate 4 has unevenness, more water molecules 11 can be attached. Accordingly, the output voltage vo can be increased, and high sensitivity can be achieved.

Furthermore, when at least the surface of the insulating substrate 4 includes a highly hydrophilic oxide, moisture can be attached easily. Incidentally, the highly hydrophilic oxide is an insulating metal oxide. That is, an oxygen atom is arranged on the surface.

Incidentally, the moisture detection element 1 according to this embodiment uses the AC voltage vi as an applied voltage as illustrated in FIG. 2A and the like. In this way, the moisture detection element 1 according to this embodiment can be speeded up. That is, when a DC voltage is used as the applied voltage, the rise of the voltage is delayed due to the capacitor component in the equivalent circuit in the moisture detection element 1 and moisture. Further, this causes a detection delay. On the other hand, when the AC voltage vi is used as the applied voltage, the influence of the capacitor component in the equivalent circuit is reduced, so that the detection delay is reduced. In particular, the detection can be speeded up by using a radio frequency (several MHz scale) as the frequency of the AC voltage vi as the applied voltage.

(During Adhesion of Dust 12)

FIG. 2C is a view illustrating an aspect in which the dust 12 adheres to the moisture detection element 1.

As illustrated in FIG. 2C, even if the dust 12 adheres to the moisture detection element 1, the dust 12 adheres to the insulating film 62, and thus a short circuit between the application electrode 2 and the detection electrode 3 due to the dust 12 can be prevented.

(Example of Arrangement of Insulating Film 62)

Figure 3A:
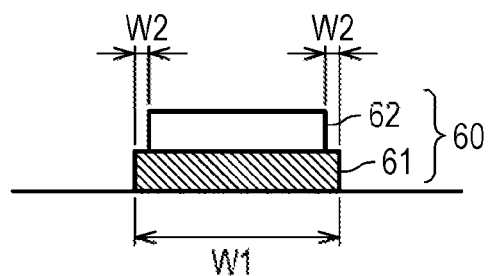
FIG. 3A is a view (part 1) illustrating an example of a width of an insulating film in an auxiliary electrode.
Figure 3B:
FIG. 3B is a view (part 2) illustrating the example of the width of the insulating film in the auxiliary electrode.
Figure 3C:
FIG. 3C is a view (part 3) illustrating the example of the width of the insulating film in the auxiliary electrode.

FIGS. 3A to 3C are views illustrating an example of the width of the insulating film 62 in the auxiliary electrode 60.

In FIG. 3A, it is satisfied that the width of the conductive film 61> the width of the insulating film 62. In FIG. 3A, W2×2 may be about 10% or less of W1.

FIG. 3B illustrates an example in which the width of the conductive film 61 is equal to the width of the insulating film 62.

FIG. 3C illustrates an example in which it is satisfied that the width of the conductive film 61< the width of the insulating film 62.

Incidentally, FIGS. 3A to 3C illustrate the relationship between the width of the conductive film 61 and the width of the insulating film 62. However, the relationship between the width of the application electrode 2 and the width of the insulating film 62, and the relationship between the detection electrode 3 and the width of the insulating film 62 is the same.

In this embodiment, as illustrated in FIG. 1, a conductive film 61 which is insulated from the application electrode 2 and the detection electrode 3 is arranged between the application electrode 2 and the detection electrode 3.

When such a conductive film 61 is arranged, the area of the portion to which moisture adheres is reduced, and the application electrode 2 and the detection electrode 3 are electrically connected even with a small amount of moisture. In addition, as described above, the insulating film 62 is provided, and thus the application electrode 2 and the detection electrode 3 are not conducted even if the dust 12 is deposited on the auxiliary electrode 60.

That is, according to the moisture detection element 1 illustrated in FIG. 1, it is possible to maintain excellent sensitivity while suppressing the occurrence of errors due to the adhesion of the dust 12.

FIG. 4 is an enlarged view of a part of the moisture detection element 1 illustrated in FIG. 1.

"a" illustrated in FIG. 4 denotes a distance between the application electrode 2 and the detection electrode 3 (this distance is referred to as an interelectrode distance), and it is desirable that a≥20 μm. Incidentally, most of the dust 12 in the atmosphere is 20 μm or less.

If a z≥20 μm, distances b between the auxiliary electrode 60 (conductive film 61) and the application electrode 2 and between the auxiliary electrode 60 and the detection electrode 3 may be any distance. However, the smaller the distances b between the auxiliary electrode 60 and the application electrode 2 and between the auxiliary electrode 60 and the detection electrode 3, the better the sensitivity. Therefore, it is desirable that the distances between the auxiliary electrode 60 and the application electrode 2 and between the auxiliary electrode 60 and the detection electrode 3 be as small as possible in consideration of the manufacturing cost.

FIG. 5 is a table showing the relationship between the interelectrode distance and the output voltage vo.

Herein, the interelectrode distance is the interelectrode distance a in FIG. 4. This table shows the results of the following processing. First, the application electrode 2 and the detection electrode 3 were electrically connected to the moisture detection element without the auxiliary electrode 60 (conductive film 61) and the moisture detection element 1 with the auxiliary electrode 60, with saturated water vapor. Then, the AC voltage vi having a peak voltage of 3 V is applied to the application electrode 2. The table shows the output voltage vo detected by the detection electrode 3 as a result. It is shown that the higher the value of the output voltage vo, the better the sensitivity.

Without the auxiliary electrode 60, when the interelectrode distance is 10 μm, an output voltage vo of 2.8 V is obtained, whereas as the interelectrode distance increases to 15 m and 20 μm, the output voltage vo decreases to 2.5 V and 2.2 V. The reason why the output voltage vo decreases despite the conduction between the application electrode 2 and the detection electrode 3 is that the resistance derived from the water molecules 11 increases as the interelectrode distance increases.

On the other hand, in the case of the moisture detection element 1 with the auxiliary electrode 60, an output of 2.8 V was obtained at an interelectrode distance of 20 μm. This is the same sensitivity as in a case where the interelectrode distance is 10 μm in the moisture detection element without the auxiliary electrode 60. However, in the moisture detection element 1 with the auxiliary electrode 60, "b" illustrated in FIG. 4 was set to b=5 μm. That is, the distances (distance b in FIG. 4) between the auxiliary electrode 60 and the application electrode 2 and between the auxiliary electrode 60 and the detection electrode 3 were each set to 5 μm.

In this way, according to the moisture detection element 1 according to this embodiment, it is possible to maintain excellent detection sensitivity while suppressing the occurrence of errors due to the dust 12. That is, the robustness of the moisture detection element 1 is improved. In addition, compared to conventional moisture detection elements, the moisture detection element 1 illustrated in FIG. 1 can be reduced in size, and it is not necessary to apply a large voltage. Thus, it is possible to realize low power consumption.

Since the dust 12 is often 20 μm or less, the occurrence of errors due to the dust 12 can be reduced by setting the interelectrode distance to 20 μm or more. In addition, according to the moisture detection element 1 illustrated in FIG. 1, the insulating film 62 is provided on the conductive film 61, the application electrode 2, and the detection electrode 3. In this way, for example, even if the dust 12 of 20 μm or more adheres to the application electrode 2 and the detection electrode 3 as illustrated in FIG. 2C, the occurrence of errors due to the dust 12 can be reduced.

(Example with Heater 8)

FIG. 6 is a view illustrating an example of a moisture detection element 1a provided with a heater 8.

In the moisture detection element 1a illustrated in FIG. 6, the heater 8 is provided between an insulating substrate 4a (4) and an insulating substrate 4b (4). In this way, the water molecules 11 adhering to the surface of the insulating substrate 4 (4a) can be evaporated by heat, and the moisture detection element 1a after the moisture adhesion can be restored to a usable state at an earliest time. Incidentally, the insulating substrates 4a and 4b may be made of the same material or different materials as long as they have insulating properties.

Incidentally, in the example of FIG. 6, the heater 8 is sandwiched between the insulating substrate 4a and the insulating substrate 4b. However, the invention is not limited thereto, and the heater 8 may be installed on the lower surface of the insulating substrate 4.

(Error Occurrence Frequency)

Figure 7A:
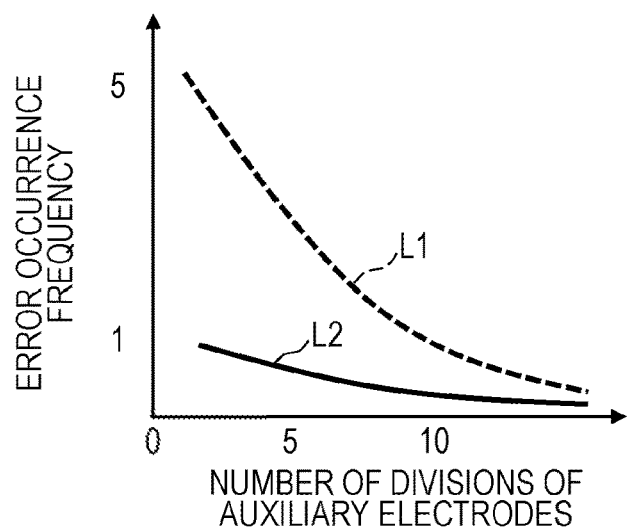
FIG. 7A is a graph showing a relationship between the number of divisions of auxiliary electrodes and an error occurrence frequency.

FIG. 7A is a graph showing a relationship between the number of divisions of the auxiliary electrodes 60 and an error occurrence frequency. In FIG. 7A, a horizontal axis indicates the number of divisions of the auxiliary electrodes 60, and a vertical axis indicates the error occurrence frequency.

Herein, the number of divisions is the number of divisions in the Y direction in FIG. 1. For example, in the example of FIG. 1, the number of divisions is "7".

In addition, a graph L1 in FIG. 7A shows the error occurrence frequency in the moisture detection element (that is, the moisture detection element in which all the conductive film 61, the application electrode 2, and the detection electrode 3 are exposed) which does not include the insulating film 62. That is, in a graph L1, it is satisfied that auxiliary electrode 60=conductive film 61.

Further, the graph L2 indicates the error occurrence frequency in the moisture detection element 1 including the insulating film 62.

As illustrated in FIG. 7A, in the moisture detection element 1 including the insulating film 62, the error occurrence frequency can be reduced significantly compared to the moisture detection element not including the insulating film 62. When the dust 12 is attached, if the insulating film 62 is not provided, the application electrode 2, the conductive film 61, and the detection electrode 3 may be short-circuited. However, when the insulating film 62 is provided, as illustrated in FIG. 2C, it is possible to prevent the application electrode 2, the conductive film 61, and the detection electrode 3 from being short-circuited.

Figure 26:
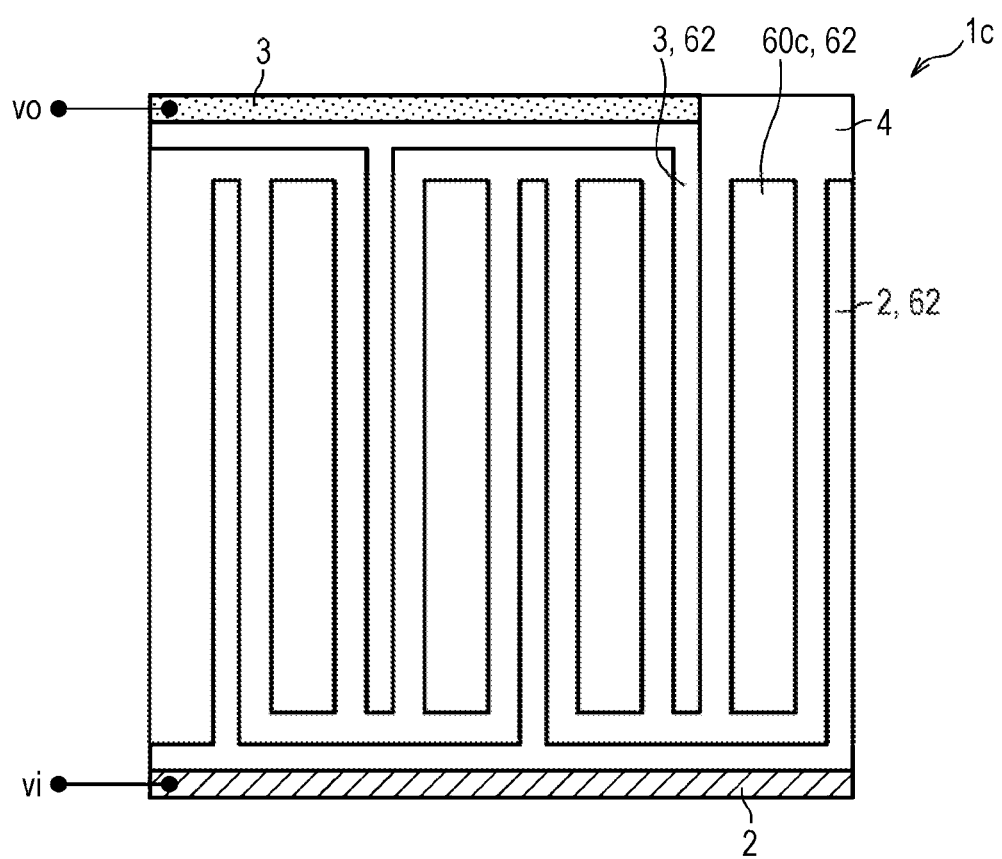
FIG. 26 is a view illustrating a second modification of the moisture detection element according to this embodiment.

As shown in the graph L2, the error occurrence frequency decreases as the number of divisions of the auxiliary electrode 60 increases. For example, as illustrated in FIG. 26, when one auxiliary electrode 60 exists between the application electrode 2 and the detection electrode 3, the application electrode 2 and the auxiliary electrode 60 may be short-circuited by one dust 12, and when the detection electrode 3 and the auxiliary electrode 60 are short-circuited by another dust 12, the application electrode 2 and the detection electrode 3 may be short-circuited.

However, as illustrated in FIG. 1, when the auxiliary electrode 60 is divided, the application electrode 2 and the detection electrode 3 are not short-circuited unless the two dusts 12 adhere to both the application electrode 2 side and the detection electrode 3 side of the same auxiliary electrode 60.

Incidentally, FIG. 7A shows the result obtained when forty moisture detection elements 1 having each division number of auxiliary electrodes 60 are used. The same applies to FIGS. 7B and 7C described below. Further, in FIG. 7A, error detection is performed for one year for the moisture detection element 1 having each division number of the auxiliary electrodes 60, and the error occurrence frequency for each moisture detection element 1 is calculated.

(Condensation Removal Time)

Figure 7B:
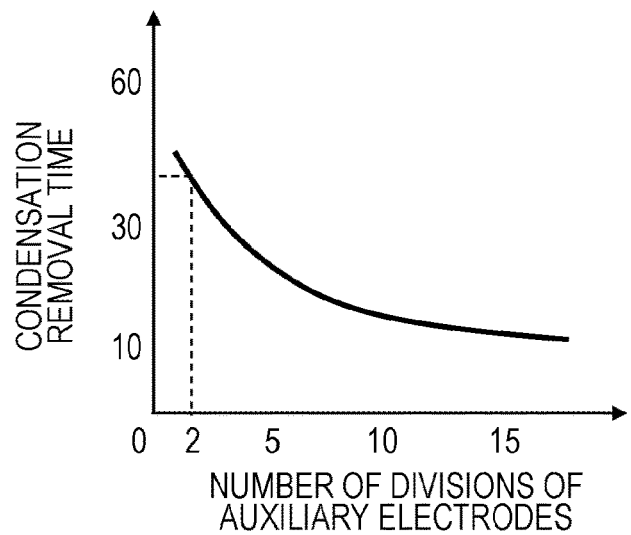
FIG. 7B is a graph showing a relationship between a condensation removal time after the heater is turned on and the number of divisions of the auxiliary electrode.

FIG. 7B is a graph showing a relationship between a condensation removal time after the heater 8 is turned on and the number of divisions of the auxiliary electrode 60. In FIG. 7B, a horizontal axis indicates the number of divisions of the auxiliary electrode 60, and a vertical axis indicates the condensation removal time after the heater 8 is turned on. Incidentally, the heater 8 is set to be 40° C.

As illustrated in FIG. 7B, the condensation removal time is shortened as the number of divisions of the auxiliary electrode 60 increases. This is because the surface area of each auxiliary electrode 60 is small. In addition, as the number of divisions of the auxiliary electrode 60 is increased, moisture is uniformly evaporated from the surface of the auxiliary electrode 60.

(Temperature Recovery Time)

Figure 7C:
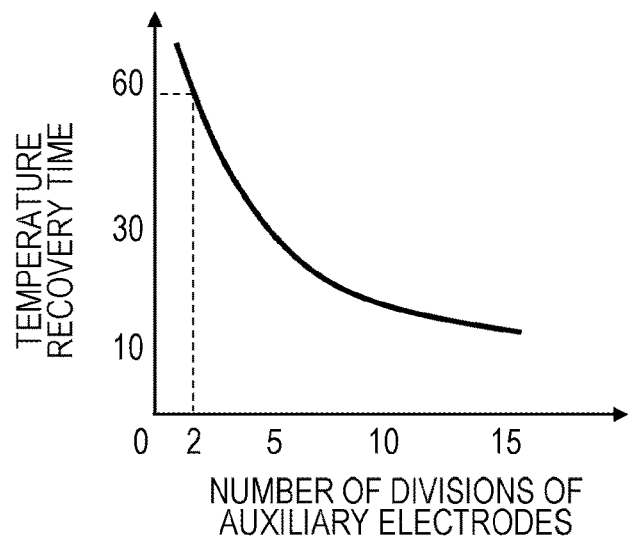
FIG. 7C is a graph showing a relationship between a temperature recovery time after the heater is turned off and the number of divisions of the auxiliary electrode.

FIG. 7C is a graph showing a relationship between a temperature recovery time after the heater 8 is turned off and the number of divisions of the auxiliary electrode 60. The temperature recovery time is a time until the surface of the insulating substrate 4 heated by the heater 8 is sufficiently cooled. Specifically, the time is a time until the insulating substrate 4 is cooled to room temperature (25° C.) after the insulating substrate 4 is sufficiently heated by the heater 8 set to 40° C.

In FIG. 7C, a horizontal axis indicates the number of divisions of the auxiliary electrode 60, and a vertical axis indicates the temperature recovery time after the heater 8 is turned off.

As illustrated in FIG. 7C, the temperature recovery time is shortened as the number of divisions of the auxiliary electrode 60 increases. This is because, as in FIG. 7B, the surface area of one auxiliary electrode 60 is small.

As illustrated in FIG. 7A, by dividing the auxiliary electrode 60, the error occurrence frequency due to the adhesion of dust 12 can be reduced. Further, as illustrated in FIGS. 7B and 7C, by dividing the auxiliary electrode 60, the heat capacity in one auxiliary electrode 60 is reduced, and the time for heat absorption and radiation is shortened. Accordingly, the re-measurement waiting time can be shortened, and the measurement efficiency can be improved.

(Method for Manufacturing Moisture Detection Element 1a)

FIGS. 8A to 8E are views illustrating a method for manufacturing the moisture detection element 1a according to this embodiment. Incidentally, FIGS. 8A to 8E illustrate the method of manufacturing the moisture detection element 1a. However, the moisture detection element 1 illustrated in FIGS. 1 and 2A also can be manufactured by the same method. Incidentally, FIGS. 8A to 8E illustrate the portion comparable to the D2-D2 cross section of FIG. 1.

Figure 8A:
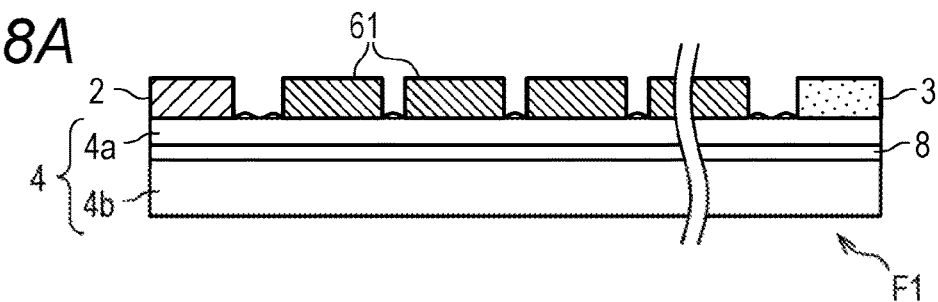
FIG. 8A is a view (part 1) illustrating a method of manufacturing the moisture detection element according to this embodiment.

First, in a state where the heater 8 is provided between the insulating substrates 4a and 4b (4), the application electrode 2, the detection electrode 3, and the conductive film 61 are formed on the insulating substrate 4a so as to have a shape as illustrated in FIG. 1 (FIG. 8A). Here, the insulating substrates 4a and 4b include a transparent insulating material such as quartz glass, polyimide, transparent plastic, or transparent metal oxide. In addition, the heater 8 also includes a transparent member such as a transparent film heater (transparent conductive film). In a state where the heater 8 is provided between the insulating substrates 4a and 4b (4), the application electrode 2, the detection electrode 3, and the conductive film 61 are formed on the insulating substrate 4a so as to have a shape as illustrated in FIG. 1, which is referred to as a moisture detection element preparation F1. Incidentally, the application electrode 2, the detection electrode 3, and the conductive film 61 include an opaque metal member.

Figure 8B:
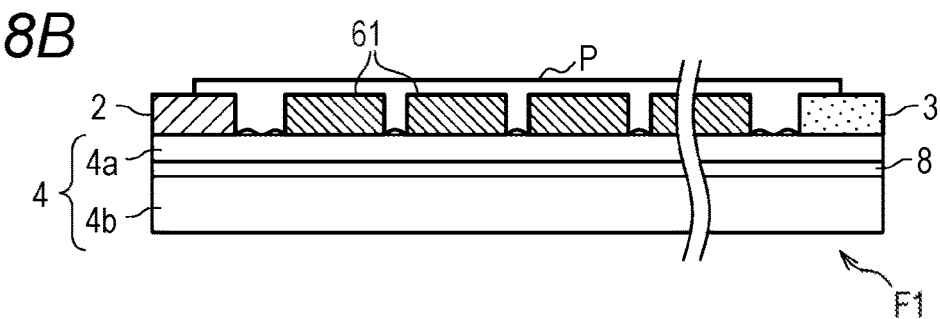
FIG. 8B is a view (part 2) illustrating the method of manufacturing the moisture detection element according to this embodiment.

A positive-type insulating photosensitive material P is applied in which portion exposed on the surface of the application electrode 2, the detection electrode 3, and the conductive film 61 of the moisture detection element preparation F1 is solubilized (FIG. 8B). Examples of the positive-type insulating photosensitive material P in which the exposed portion is solubilized include photosensitive polyimide.

Figure 8C:
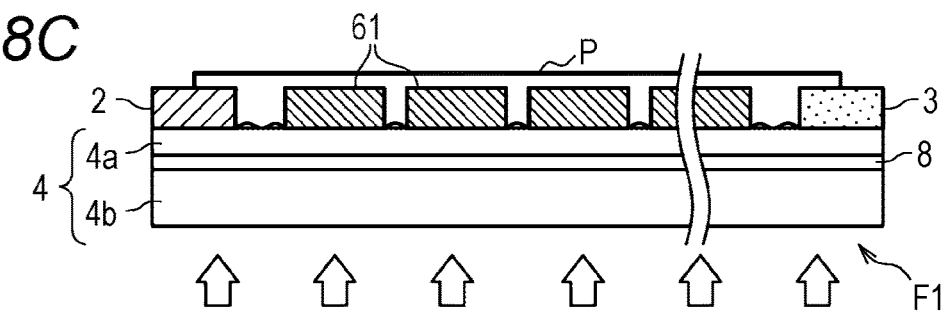
FIG. 8C is a view (part 3) illustrating the method of manufacturing the moisture detection element according to this embodiment.

Then, as illustrated in FIG. 8C, exposure (white arrow) is performed from the back side of the moisture detection element preparation F1 coated with the positive-type insulating photosensitive material P in which the exposed portion is solubilized. Herein, the back side of the moisture detection element preparation F1 is the side on which the application electrode 2, the detection electrode 3, and the conductive film 61 are not formed.

Since the insulating substrates 4a and 4b and the heater 8 are transparent, and the application electrode 2, the detection electrode 3 and the conductive film 61 are opaque, the application electrode 2, the detection electrode 3 and the conductive film 61 serve as a mask. As a result, as illustrated in FIG. 8D, the portion of the insulating photosensitive material P that is not applied on the application electrode 2, the detection electrode 3, and the conductive film 61 becomes soluble (portion M).

After this process, on the surface side of the insulating photosensitive material P, a photomask is formed in a portion other than the wiring connection portion (not illustrated) of the application electrode 2 and the detection electrode 3. Herein, the surface side is the side on which the application electrode 2, the detection electrode 3, and the conductive film 61 are formed. In addition, the wiring connection portion is a portion where the wiring is connected in the application electrode 2 and the detection electrode 3. After that, exposure is performed again from the surface side, so that the insulating photosensitive material P on the wiring connection portion in the application electrode 2 and the detection electrode 3 becomes soluble. By performing such a process and washing away the soluble insulating photosensitive material P described later, the insulating film 62 cannot be formed on the places where the wiring is connected in the application electrode 2 and the detection electrode 3. In other words, the place where the wiring is connected in the application electrode 2 and the detection electrode 3 is exposed, and the wiring can be connected to the application electrode 2 and the detection electrode 3.

Figure 8D:
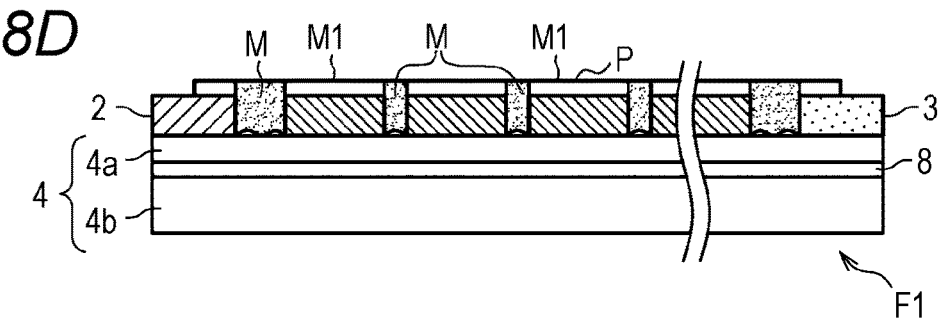
FIG. 8D is a view (part 4) illustrating the method of manufacturing the moisture detection element according to this embodiment.
Figure 8E:
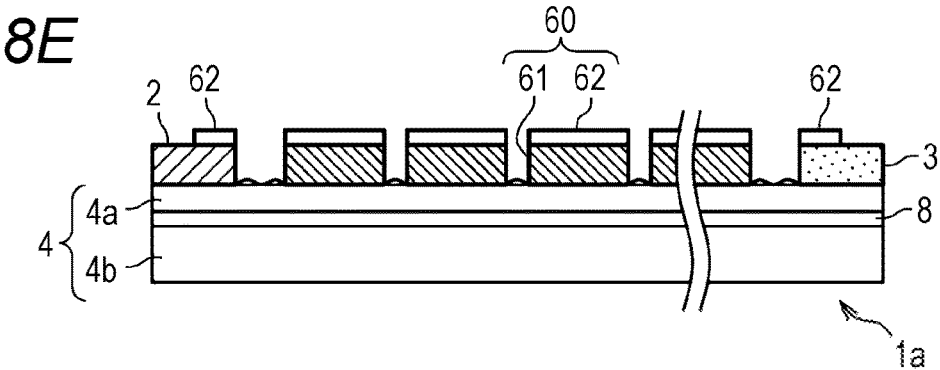
FIG. 8E is a view (part 5) illustrating the method of manufacturing the moisture detection element according to this embodiment.

Thereafter, baking is performed to cure the insoluble part of the insulating photosensitive material P (reference numeral M1 in FIG. 8D). Then, by washing away the soluble insulating photosensitive material P, the insulating photosensitive material P (that is, insulating film 62) is formed on the application electrode 2, the detection electrode 3, and the conductive film 61 as illustrated in FIG. 8E.

According to the manufacturing method illustrated in FIGS. 8A to 8E, the moisture detection element 1a having the insulating film 62 can be manufactured with high accuracy by a simple method.

The manufacturing method is not limited to the manufacturing method illustrated in FIGS. 8A to 8E, and the insulating film 62 may be formed by general photolithography. That is, the moisture detection elements 1 and 1a may be manufactured by resist formation→surface exposure using a photomask→development→etching (or processing). In this case, the heater 8 and the insulating substrate 4 need not be transparent members. When the insulating film 62 includes a metal oxide film, the insulating film 62 is formed by such general photolithography.

[Exhalation Sensor 100]

Next, an exhalation sensor 100 using the moisture detection element 1 will be described.

(Planar Arrangement Structure)

Figure 9:
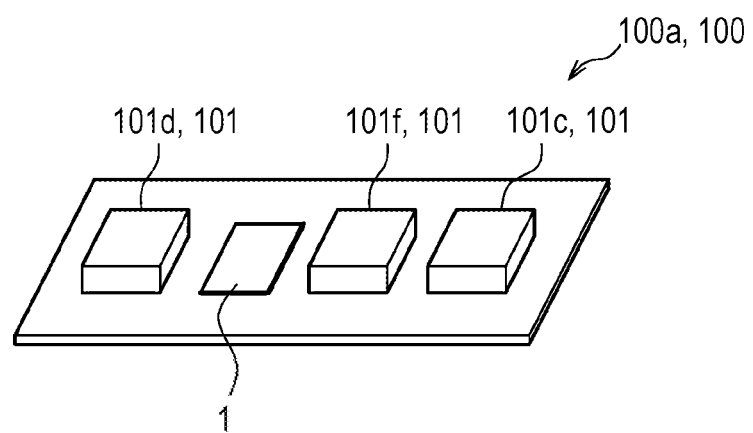
FIG. 9 is a view illustrating a basic configuration example of an exhalation sensor 100 having a planar arrangement structure.

FIG. 9 is a view illustrating a basic configuration example of the exhalation sensor 100 having a planar arrangement structure.

In an exhalation sensor (exhaled gas detector) 100a (100) having a planar arrangement structure illustrated in FIG. 9, the moisture detection element 1 is arranged on a circuit board having a planar structure. Furthermore, in the exhalation sensor 100a, a plurality of types of small gas sensors (gas detection part) 101 are arranged around the moisture detection element 1. The moisture detection element 1 is illustrated in any of FIGS. 1 and 6 and FIGS. 24A to 28B described later.

The gas sensor 101 arranged around the moisture detection element 1 is a gas sensor 101c for alcohol, a gas sensor 101d for acetaldehyde, a gas sensor 101f for hydrogen, and the like. Incidentally, although various substances are contained in alcohol, in this embodiment, an example using ethanol is described.

In addition, the gas sensor 101c for alcohol (ethanol) detects whether the subject is drunk (presence/absence of alcohol in exhalation) and the like. In addition, the gas sensor 101d for acetaldehyde detects drunkenness by detecting a metabolite of alcohol, and the gas sensor 101f for hydrogen detects the presence or absence of activation of the digestive system. Incidentally, here, "presence or absence" refers to whether or not a predetermined amount or more of a component is included in the exhalation.

Incidentally, the moisture detection element 1 and the gas sensors 101c, 101d, and 101f do not have to be arranged as illustrated in FIG. 9. However, it is preferable that the moisture detection element 1 is arranged as close to the center of the exhalation sensor 100a as possible.

Figure 10:
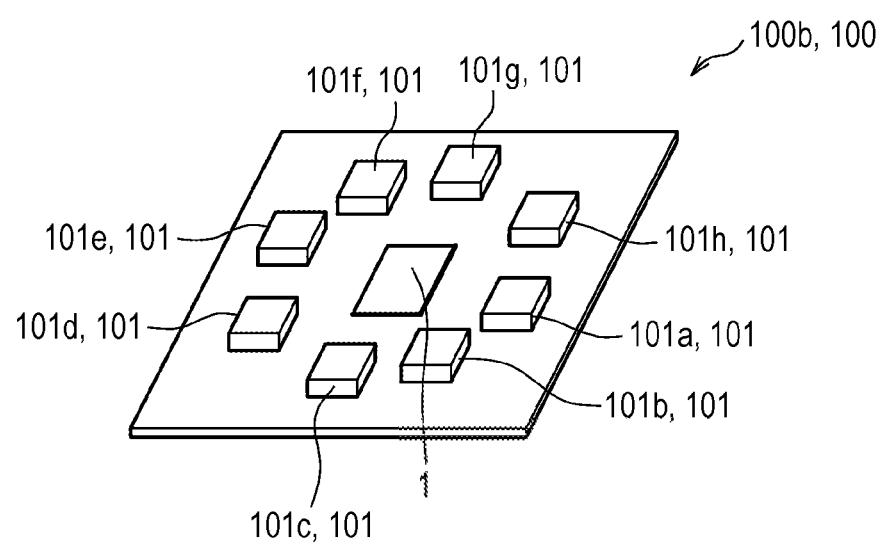
FIG. 10 is a view illustrating a configuration example of the exhalation sensor 100 for healthcare having a planar arrangement structure.

FIG. 10 is a view illustrating a configuration example of the exhalation sensor 100 for healthcare having a planar arrangement structure. In FIG. 10, the same components as those in FIG. 9 are denoted by the same reference numerals, and the description is omitted.

In an exhalation sensor (gas detector) 100b (100) having the planar arrangement structure illustrated in FIG. 10, the moisture detection element 1 is arranged at the center of the circuit board having a planar structure. Furthermore, in the exhalation sensor 100b, a plurality of types of small gas sensors (gas detection parts) 101 are arranged around the moisture detection element 1. The moisture detection element 1 is illustrated in any of FIGS. 1 and 6 and FIGS. 24A to 28B described later.

The gas sensor 101 arranged around the moisture detection element 1 includes a gas sensor 101a for carbon monoxide, a gas sensor 101b for nitric oxide, a gas sensor 101c for alcohol, a gas sensor 101d for acetaldehyde, a gas sensor 101e for acetone, and a gas sensor 101f for hydrogen, a gas sensor 101g for hydrogen sulfide, a gas sensor 101h for ammonia, and the like. Incidentally, although various substances are contained in alcohol, in this embodiment, an example using ethanol is described.

Incidentally, the moisture detection element 1 and the gas sensors 101a to 101h need not be arranged as illustrated in FIG. 10. However, it is preferable that the moisture detection element 1 be arranged as close to the center of the exhalation sensor 100b as possible.

The gas sensor 101a for carbon monoxide can detect the presence or absence of smoking, the gas sensor 101b for nitric oxide can detect the presence or absence of inflammation in the respiratory system such as pneumonia, and the gas sensor 101e for acetone can detect the presence or absence of diabetes. In addition, the gas sensor 101g for hydrogen sulfide can detect the presence or absence of bad breath, and the gas sensor 101h for ammonia can detect the presence or absence of *Helicobacter pylori* or liver disease. Incidentally, here, "presence or absence" refers to whether or not a predetermined amount or more of a component is included in the exhalation.

In FIG. 10, the configuration includes eight types of gas sensors 101 but does not have to include all of them. A configuration including one type or several types of gas sensors 101 may be used depending on the purpose. Alternatively, the used gas sensor 101 may be switched according to the purpose. Furthermore, the invention is not limited to the gas sensor 101 used in the example illustrated in FIG. 10. For example, a gas sensor 101 for carbon dioxide may be arranged.

According to the exhalation sensors 100a and 100b illustrated in FIGS. 9 and 10 respectively, gas detection can be performed while determining whether or not the exhalation introduced by the moisture detection element 1 is human exhalation as will be described later.

[Example of Package 200]

Next, an example of a package 200 of the exhalation sensor 100 according to this embodiment will be described with reference to FIGS. 11A and 11B.

Figure 11A:
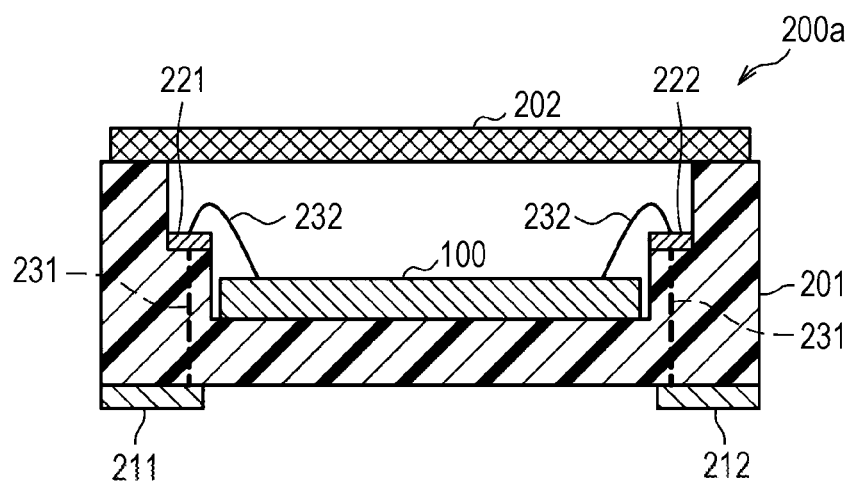
FIG. 11A is a schematic cross-sectional view of a package 200a using wire bonding.

FIG. 11A is a schematic cross-sectional view of an exhalation sensor package (hereinafter referred to as a package 200a) using wire bonding.

The package 200a has a box-shaped main body 201 and a lid 202. The exhalation sensor 100 is installed inside the ceramic main body 201. In addition, the main body 201 includes an outer application electrode 211 and an outer detection electrode 212 on the outside. Further, the main body 201 has an inner application electrode 221 and an inner detection electrode 222 on the inside. The outer application electrode 211 and the inner application electrode 221 are connected by a main body wiring 231 built in the main body 201. Similarly, the outer detection electrode 212 and the inner detection electrode 222 are connected by the main body wiring 231 built in the main body 201.

Further, the inner application electrode 221 is connected to the application electrode 2 (see FIGS. 1 to 2B and the like) of the moisture detection element 1 by wire bonding using the conductive wire 232 and wiring on the circuit board of the exhalation sensor 100. Similarly, the inner detection electrode 222 is connected to the detection electrode 3 (see FIGS. 1 to 2B and the like) of the moisture detection element 1 by wire bonding using the conductive wire 232 and wiring on the circuit board of the exhalation sensor 100.

The lid 202 is provided with a mesh and prevents the dust 12 and the like existing outside the package 200a from adhering to the moisture detection element 1. When a mesh is provided in the lid 202 as above, the dust 12 can be prevented from adhering to the moisture detection element 1, and the occurrence of errors due to the dust 12 is further reduced.

Figure 11B:
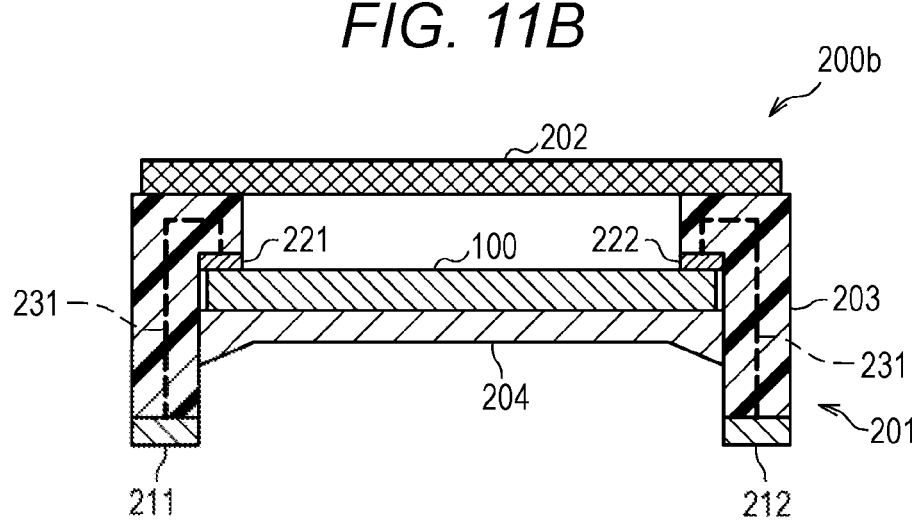
FIG. 11B is a schematic cross-sectional view of a package 200b using a flip chip.

FIG. 11B is a schematic cross-sectional view of an exhalation sensor package (hereinafter referred to as a package 200b) using a flip chip.

The package 200b includes a box-shaped main body 201b and a lid 202. The main body 201b further includes a side wall 203 and a bottom 204. Both the side wall 203 and the bottom 204 are made of ceramic. Incidentally, as illustrated in FIG. 11B, the side wall 203 also serves as a leg.

The exhalation sensor 100 is installed so as to be placed on the bottom 204. In addition, the side wall 203 includes the outer application electrode 211 and the outer detection electrode 212 on the outside. Further, the side wall 203 includes the inner application electrode 221 and the inner detection electrode 222 on the inside. The outer application electrode 211 and the inner application electrode 221 are connected by the main body wiring 231 built in the side wall 203. Similarly, the outer detection electrode 212 and the inner detection electrode 222 are connected by the main body wiring 231 built in the side wall 203.

The inner application electrode 221 is connected to an application terminal (not illustrated) on the circuit board of the exhalation sensor 100 in a flip-chip format. This application terminal is connected to the application electrode 2 (see FIGS. 1 and 2A and the like) of the moisture detection element 1 via wiring on the circuit board of the exhalation sensor 100. Similarly, the inner detection electrode 222 is connected to a detection terminal (not illustrated) on the circuit board of the exhalation sensor 100 in a flip chip format. This detection terminal is connected to the detection electrode 3 (see FIGS. 1 and 2A and the like) of the moisture detection element 1 via the wiring on the circuit board of the exhalation sensor 100.

Incidentally, similarly with FIG. 11A, the lid 202 is provided with a mesh. Since this mesh has the same configuration and effect as in FIG. 11A, the description thereof is omitted here.

Figure 22:
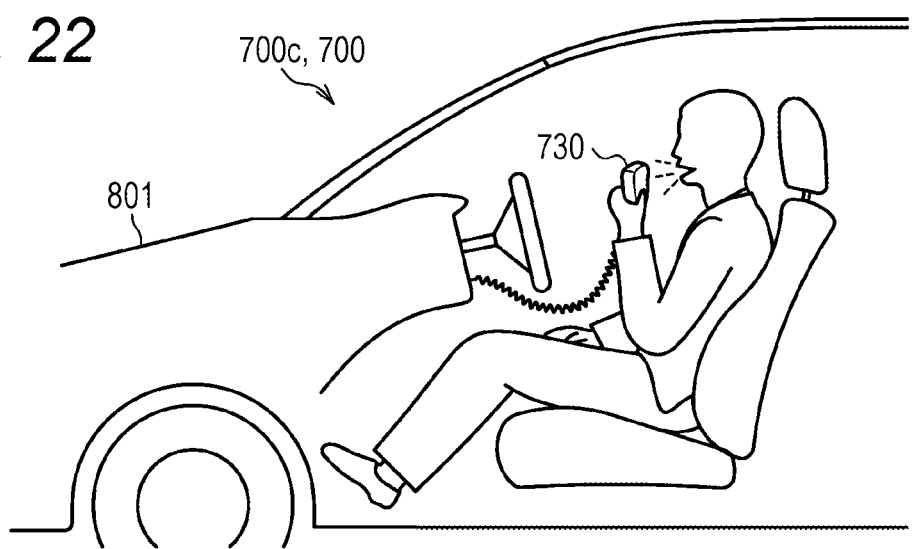
FIG. 22 is a view illustrating an example of an exhalation test device 700c which is provided in an automobile 801.

Incidentally, as illustrated in FIG. 22, when an exhalation introduction device 730 that introduces exhalation at the mouth is provided with a mesh, the lid 202 can be omitted in the packages 200a and 200b.

[Exhalation Test System Z]

Figure 12:
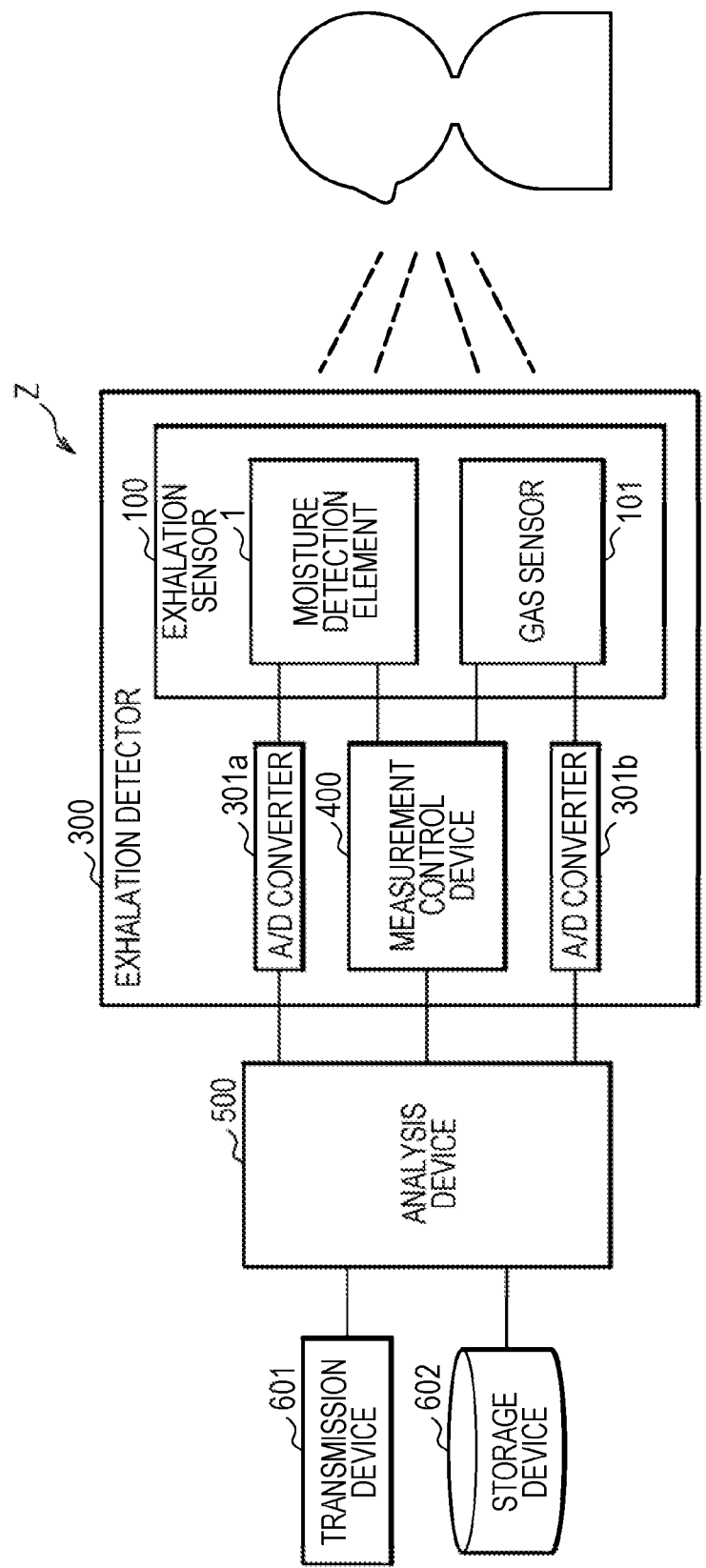
FIG. 12 is a view illustrating an example of functional blocks of an exhalation test system Z according to this embodiment.

FIG. 12 is a view illustrating an example of functional blocks of an exhalation test system Z according to this embodiment.

The exhalation test system Z includes an exhalation detector 300, an analysis device (analysis part) 500, a transmission device 601, and a storage device 602.

The exhalation detector 300 includes an exhalation sensor 100 and a measurement control device 400. The exhalation sensor 100 includes the moisture detection element 1 and the gas sensor 101. However, since the description has been given in FIGS. 9 and 10, the description thereof is omitted here.

The measurement control device 400 converts the frequency of the AC power supply 410 (see FIG. 13) and outputs it.

In addition, the exhalation detector 300 converts the acquired analog signal into a digital signal by A/D (Analog/Digital) converters 301a and 301b and outputs the digital signal to the analysis device 500. The acquired analog signal is a voltage signal of the output voltage vo acquired from the moisture detection element 1 or a detection signal acquired from the gas sensor 101.

The analysis device 500 acquires a voltage signal of the output voltage vo from the moisture detection element 1 in the exhalation sensor 100 and acquires a detection signal from the gas sensor 101. Then, the analysis device 500 analyzes the gas content rate in the exhalation on the basis of the output voltage vo acquired from the moisture detection element 1, the detection signal acquired from the gas sensor 101, and the like. Incidentally, in this embodiment, the analysis device 500 acquires the output voltage vo and the detection signal from the exhalation sensor 100. However, the invention is not limited thereto. The measurement control device 400 may acquire the output voltage vo and the detection signal from the exhalation sensor 100 and transfer the acquired output voltage vo and the detection signal to the analysis device 500.

The storage device 602 is a database server or the like. The storage device 602 holds the output voltage vo acquired by the analysis device 500 from the moisture detection element 1 and the detection signal acquired from the gas sensor 101 together with the test time or holds the analysis result by the analysis device 500.

The transmission device 601 notifies the analysis result (such as information about the driver state) by the analysis device 500 to a central information center (not illustrated) or the like.

(Measurement Control Device 400)

Figure 13:
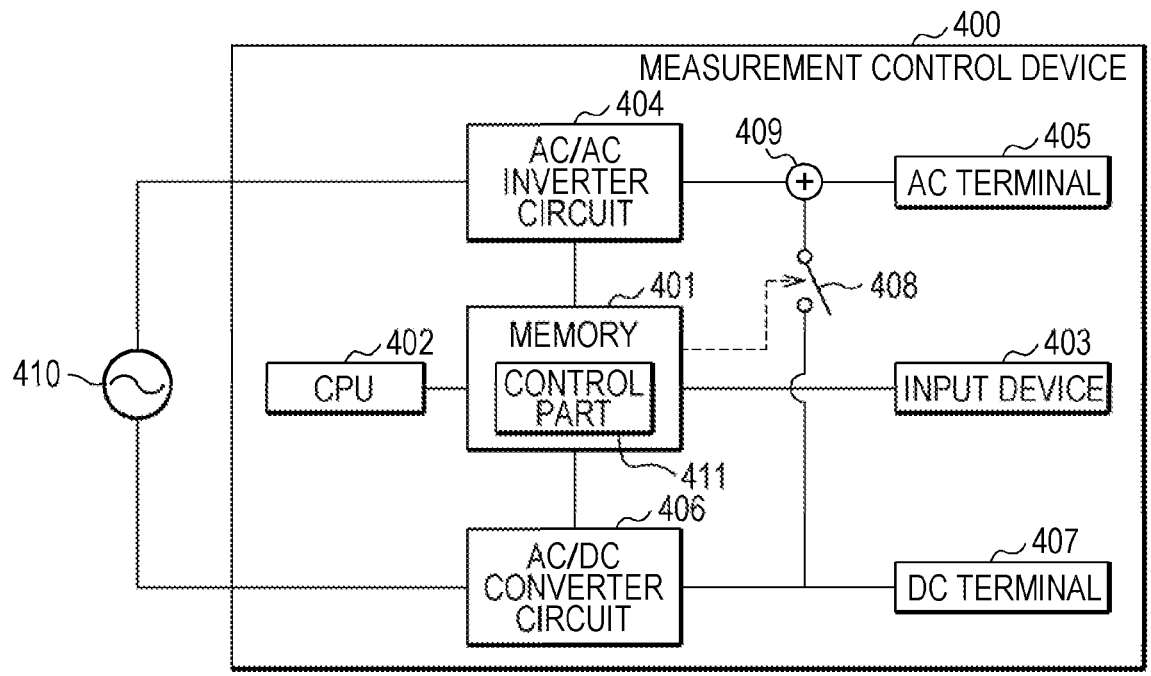
FIG. 13 is a functional block view illustrating a configuration example of a measurement control device 400 used in this embodiment.

FIG. 13 is a functional block view illustrating a configuration example of the measurement control device 400 used in this embodiment.

The measurement control device 400 includes a memory 401, a central processing unit (CPU) 402, an input device 403, and an AC/AC inverter circuit 404. Further, the measurement control device 400 includes an AC terminal 405, an AC/DC converter circuit 406, and a DC terminal 407.

In the memory 401, a control part 411 is embodied by executing a program by the CPU 402.

The control part 411 sends an instruction to the AC/AC inverter circuit 404 and the AC/DC converter circuit 406 on the basis of the information input via the input device 403.

The AC/AC inverter circuit 404 converts the frequency and voltage of the AC voltage input from the AC power supply 410 on the basis of the instruction sent from the control part 411 and outputs the converted voltage to the AC terminal 405. The moisture detection element 1 is connected to the AC terminal 405.

In addition, the AC/DC converter circuit 406 converts the voltage of the AC voltage input from the AC power supply 410 on the basis of the instruction sent from the control part 411 and further converts the alternating current into a direct current to output the direct current to the DC terminal 407. The gas sensor 101 (see FIG. 12) is connected to the DC terminal 407.

The output of the AC/DC converter circuit 406 is connected via a switch 408 to an adder 409 provided on the output side of the AC/AC inverter circuit 404. The opening and closing of the switch 408 is controlled by the control part 411. Prior to the introduction of exhalation, the switch 408 is in an ON state. At this time, when the potential difference between the DC voltage Vi applied to the moisture detection element 1 and the output voltage Vo is equal to or less than a predetermined value (S202 in FIG. 17→Yes), the voltage in which the DC voltage is biased to the AC voltage with the switch 408 turned ON is applied to the application electrode 2 for a predetermined time. The case where the potential difference between the DC voltage Vi applied to the moisture detection element 1 and the output voltage Vo is equal to or smaller than a predetermined value is a case where condensation occurs (details will be described later).

In other cases, the switch 408 is in an OFF state.

Incidentally, when condensation occurs in the moisture detection element 1, the output voltage of the DC terminal 407 may be directly applied to the moisture detection element 1.

The configuration of the measurement control device 400 illustrated in FIG. 13 is an example and is not limited to the configuration illustrated in FIG. 13. For example, an AC signal (AC voltage vi) may be generated using a crystal oscillator.

In addition, the measurement control device 400 illustrated in FIG. 13 corresponds to the power supply 5 in FIGS. 2A and 2B.

(Analysis Device 500)

Figure 14:
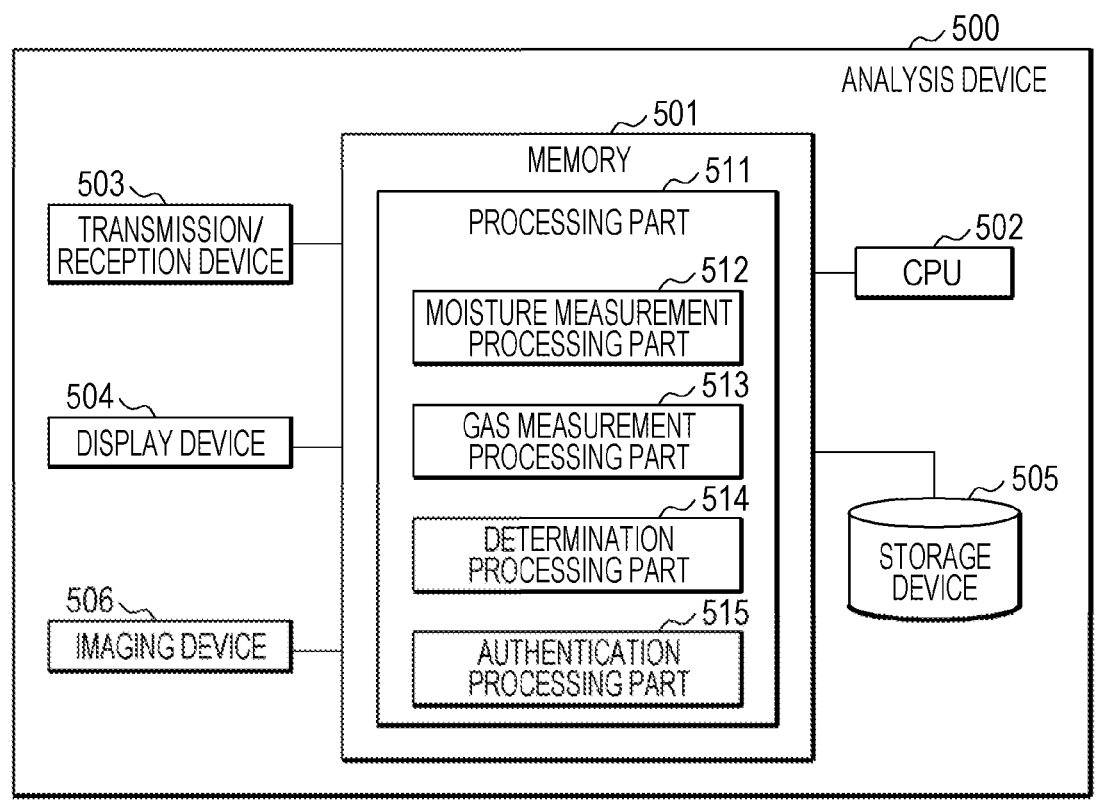
FIG. 14 is a functional block view illustrating a configuration example of an analysis device 500 used in this embodiment.

FIG. 14 is a functional block view illustrating a configuration example of the analysis device 500 used in this embodiment.

The analysis device 500 is, for example, a personal computer (PC), and includes a memory 501, a CPU 502, a transmission/reception device 503, and a display device (display part) 504. Furthermore, the analysis device 500 includes a storage device 505 such as a hard disk drive (HDD), an imaging device (imaging part) 506, and the like. Incidentally, the imaging device 506 can be omitted when the spoofing prevention processing described later is not performed.

A program stored in the storage device 505 is loaded into the memory 501. Then, the loaded program is executed by the CPU 502, thereby realizing a processing part 511 and parts 512 to 515 configuring the processing part 511.

A moisture measurement processing part 512 performs processing related to the measurement of moisture contained in exhalation on the basis of the detection signal sent from the moisture detection element 1 (see FIG. 12).

A gas measurement processing part 513 performs processing related to measurement of various gases contained in exhalation on the basis of the detection signal sent from the gas sensor 101 (see FIG. 12).

On the basis of the measurement result of the gas measurement processing part 513, a determination processing part 514 determines, for example, whether or not the subject is drunk.

An authentication processing part 515 performs spoofing prevention processing described later.

Incidentally, when the exhalation test system Z does not measure gas, the gas measurement processing part 513 can be omitted.

Incidentally, in the exhalation test system Z illustrated in FIG. 12, the exhalation detector 300, the analysis device 500, the transmission device 601, and the storage device 602 are separate devices, but the invention is not limited to this. For example, at least two of the exhalation detector 300, the analysis device 500, the transmission device 601, and the storage device 602 may be one device.

For example, the exhalation detector 300, the analysis device 500, the transmission device 601, and the storage device 602 may all be provided in one device.

Alternatively, the analysis device 500, the transmission device 601, and the storage device 602 may be provided in one device.

[Flowchart]

Next, a processing procedure of the exhalation test system Z according to this embodiment will be described with reference to FIGS. 15 to 19. Reference is made to FIGS. 12 to 14 as appropriate.

(Exhalation Detection Processing)

Figure 15:
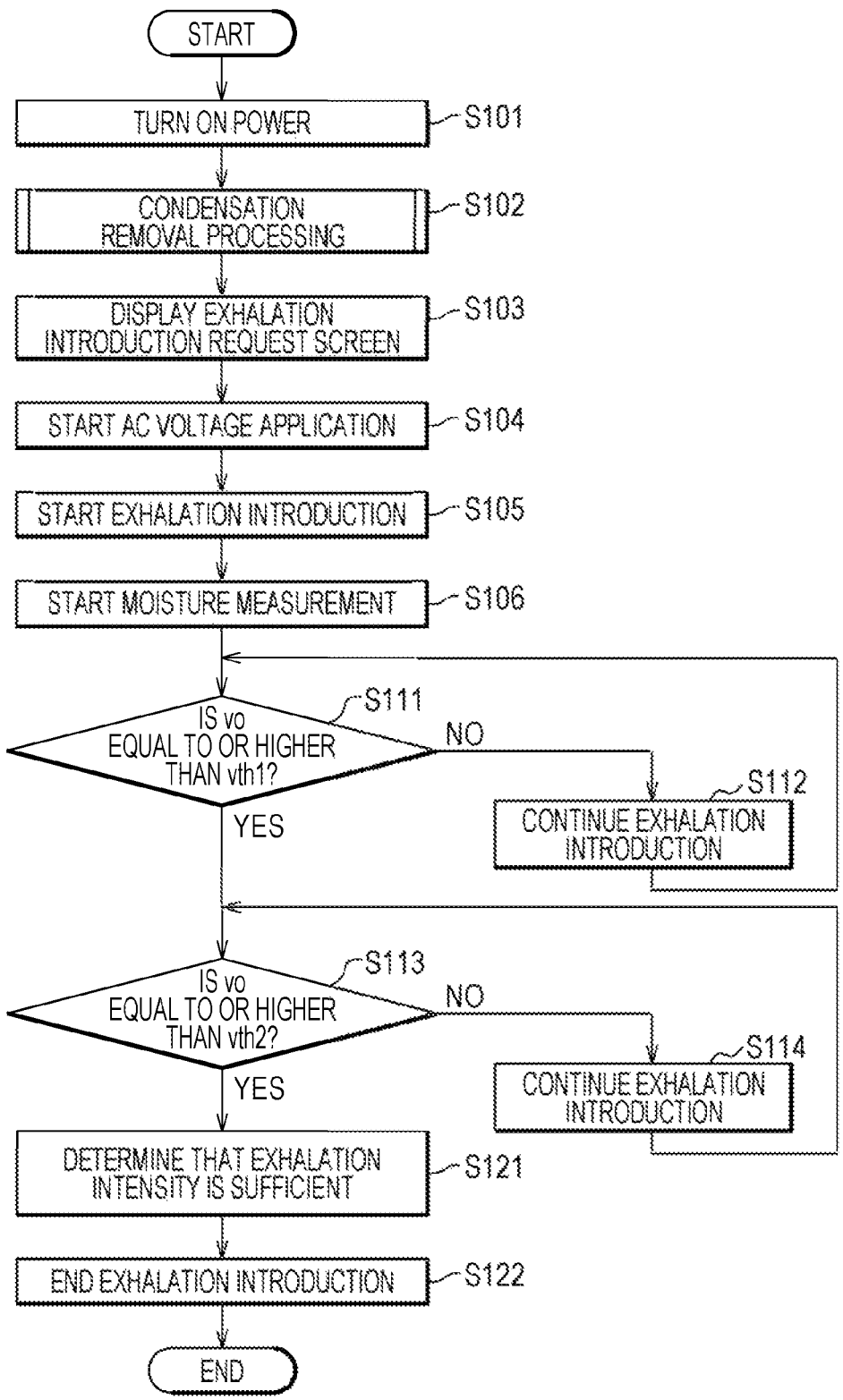
FIG. 15 is a flowchart illustrating a procedure of exhalation detection processing performed in this embodiment.

FIG. 15 is a flowchart showing the procedure of the exhalation detection processing performed in this embodiment.

First, when the user turns on the power of the exhalation test system Z (S101), the exhalation test system Z performs a condensation removal processing (S102). The condensation removal processing will be described later.

When the condensation removal processing is completed, the moisture measurement processing part 512 displays a screen (exhalation introduction request screen) for prompting the user to introduce exhalation on the display device 504 (S103).

Then, application of the AC voltage vi to the application electrode 2 is started (S104). Incidentally, the applied AC voltage vi is output from the AC terminal 405 of the measurement control device 400.

Thereafter, when the subject introduces exhalation into the exhalation introduction port, exhalation introduction is started (S105).

Then, the moisture measurement processing part 512 starts measuring the output voltage vo from the moisture detection element 1, whereby the moisture measurement is started (S106). At this time, the moisture measurement processing part 512 calculates the difference in voltage value from time 0 to the current time as the output voltage vo.

Thereafter, the moisture measurement processing part 512 determines whether or not the output voltage vo from the moisture detection element 1 is equal to or higher than the first threshold value vth1 (S111).

As a result of step S111, when the output voltage vo from the moisture detection element 1 is less than the first threshold value vth1 (S111→No), it is assumed that the exhalation intensity is insufficient, and the introduction of exhalation is continued in the subject (S112). Then, the moisture measurement processing part 512 returns the process to step S111.

As a result of step S11, when the output voltage vo is equal to or higher than the first threshold value vth1 (S111→Yes), the moisture measurement processing part 512 determines whether or not the output voltage vo from the moisture detection element 1 is equal to or higher than the second threshold value vth2 (S113). Incidentally, it is satisfied that first threshold value vth1<second threshold value vth2. Further, the output voltage vo is actually an AC voltage, and thus the determination in step S112 is performed when the moisture measurement processing part 512 determines whether or not the number of times that the voltage peak of the output voltage vo is equal to or greater than the second threshold value vth2 exceeds a predetermined number of times. This will be described later.

As a result of step S113, when the output voltage vo is less than the second threshold value vth2 (S113→No), it is assumed that the exhalation intensity is insufficient, and the moisture measurement processing part 512 continues the introduction of exhalation to the subject (S114). Then, the moisture measurement processing part 512 returns the process to step S113.

As a result of step S113, when the output voltage vo is equal to or higher than the second threshold value vth2 (S113→Yes), the moisture measurement processing part 512 determines that the exhalation intensity is sufficient (S121). Thereafter, the subject ends the introduction of exhalation (S122). At this time, the exhalation detector 300 notifies the subject that the introduction of exhalation is to be terminated by a buzzer, sound, screen display, or the like.

Figure 16:
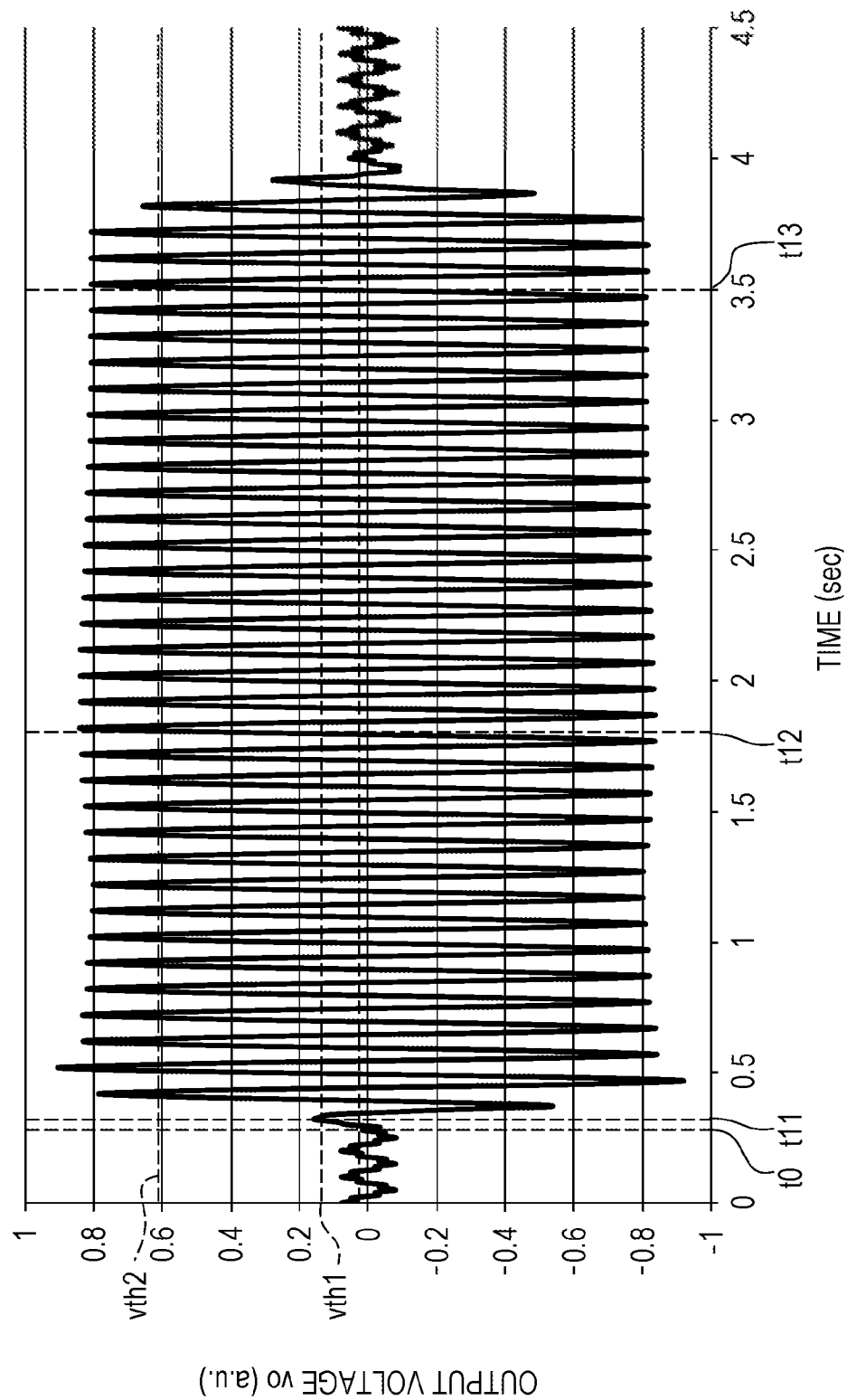
FIG. 16 is a graph illustrating the time change of the output voltage vo.

FIG. 16 is a graph illustrating the time change of the output voltage vo of the moisture detection element 1.

In FIG. 16, a horizontal axis represents time (sec), and a vertical axis represents output voltage vo (arbitrary unit).

First, when the subject starts introducing exhalation at time t0 (step S105 in FIG. 15), the output voltage vo starts to increase, and at time t11, the output voltage vo exceeds the first threshold value vth1 (step S111 in FIG. 15; Yes). Thereafter, the output voltage vo continues to increase, and the voltage peak exceeds the second threshold value vth2 fifteen times at time t12 (step S113 in FIG. 15; Yes). The number of times can be arbitrarily determined. The number of times depends on the frequency, but the number of peaks is approximately equivalent to one to three seconds after the output voltage vo exceeds the first threshold value vth1.

In addition, the second threshold value vth2 is an output voltage vo sufficient to confirm that moisture is contained in the introduced air (exhalation).

Thereafter, at time t13, the subject ends the exhalation introduction (step S122 in FIG. 15).

(Condensation Removal Processing)

Figure 17:
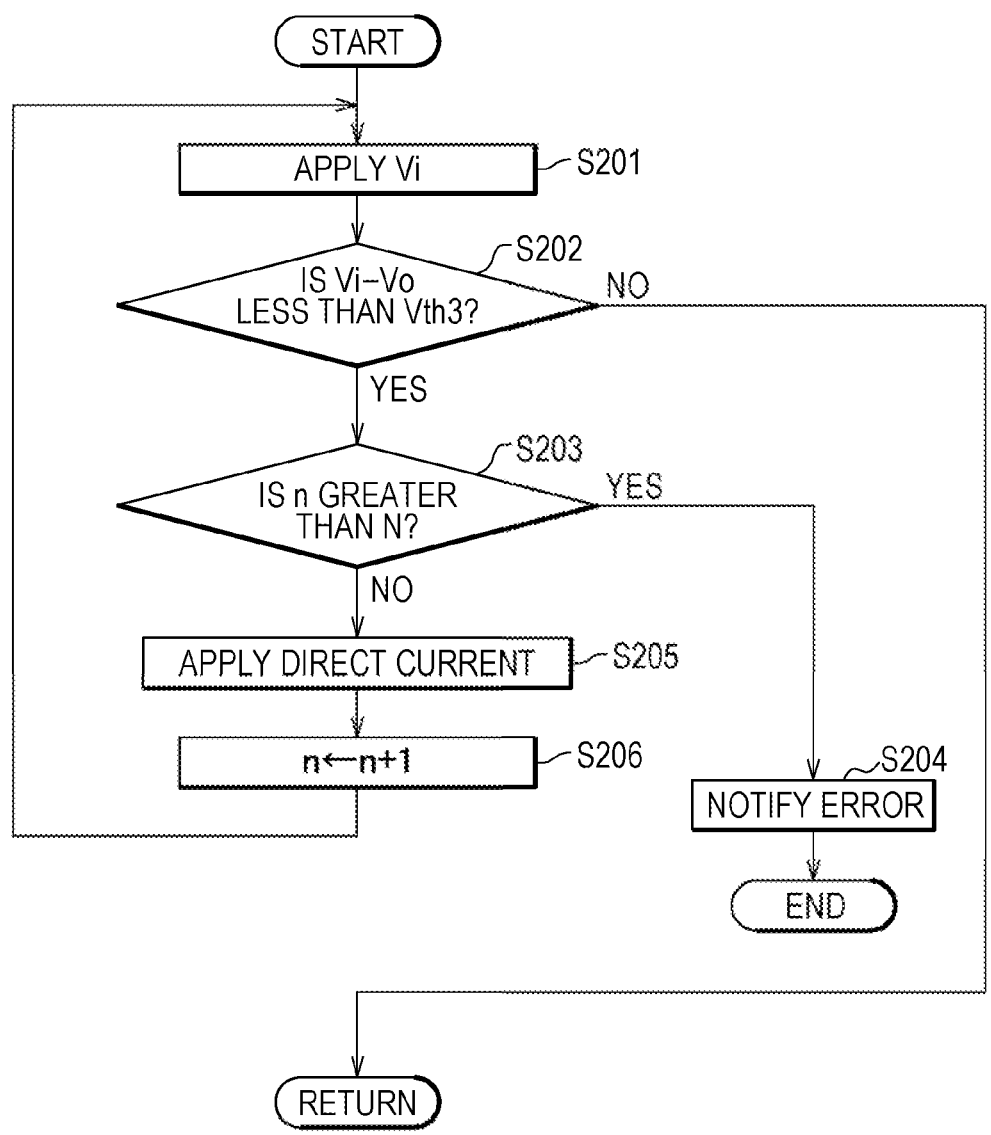
FIG. 17 is a flowchart illustrating a procedure of condensation removal processing performed in this embodiment.

FIG. 17 is a flowchart illustrating the procedure of condensation removal processing (S102 in FIG. 15) performed in this embodiment.

First, the DC voltage Vi is applied to the application electrode 2 (S201), and the moisture measurement processing part 512 is configured to measure the output voltage (DC) Vo at the detection electrode 3. As described above, the DC voltage Vi applied in step S201 is a voltage output from the AC terminal 405 of the measurement control device 400. Incidentally, the voltage actually applied in step S201 is obtained by biasing a DC voltage to an AC voltage as described above.

Then, the moisture measurement processing part 512 determines whether or not Vi-Vo is less than the third threshold value Vth3 (S202). In addition, Vi and Vo indicate bias voltage values.

As a result of step S202, when Vi-Vo is greater than or equal to the third threshold value Vth3 (S202→No), the moisture measurement processing part 512 determines that no condensation has occurred or that condensation is removed, and the procedure returns to the processing in FIG. 15.

As a result of step S202, when Vi-Vo is less than the third threshold value Vth3 (S202→Yes), the moisture measurement processing part 512 determines that condensation occurs.

Then, the moisture measurement processing part 512 determines whether or not the number of times of application n is greater than the predetermined number N (S203).

As a result of step S203, when the number n of times of application is larger than the predetermined number N (S203→Yes), the moisture measurement processing part 512 gives an error notification (S204). In the error notification, information indicating that an error is detected may be displayed on the display device 504, or the error notification may be issued from an alarm device (not illustrated). After the error notification, the exhalation test system Z ends the processing.

As a result of step S203, when the number n of application is equal to or less than the predetermined number N (S203→No), the moisture measurement processing part 512 applies a direct current to the moisture detection element 1 for a certain period of time (S205). Incidentally, as described above, in step S205, an alternating current biased with a direct current is actually applied.

Thereafter, the moisture measurement processing part 512 adds 1 to n (n←n+1) (S206), and the procedure returns to step S201.

In this way, the direct current corresponding to the bias flows through the water molecules 11 and the conductive film 6, and the water molecules 11 are evaporated by Joule heat generated at that time. In this way, the condensation can be removed. In other words, the path of the water molecule 11 is regarded as a current path, and by passing a direct current through this path, the water molecule 11 is evaporated by Joule heat derived from the resistance of the water molecule 11.

(Gas Detection Processing)

Figure 18A:
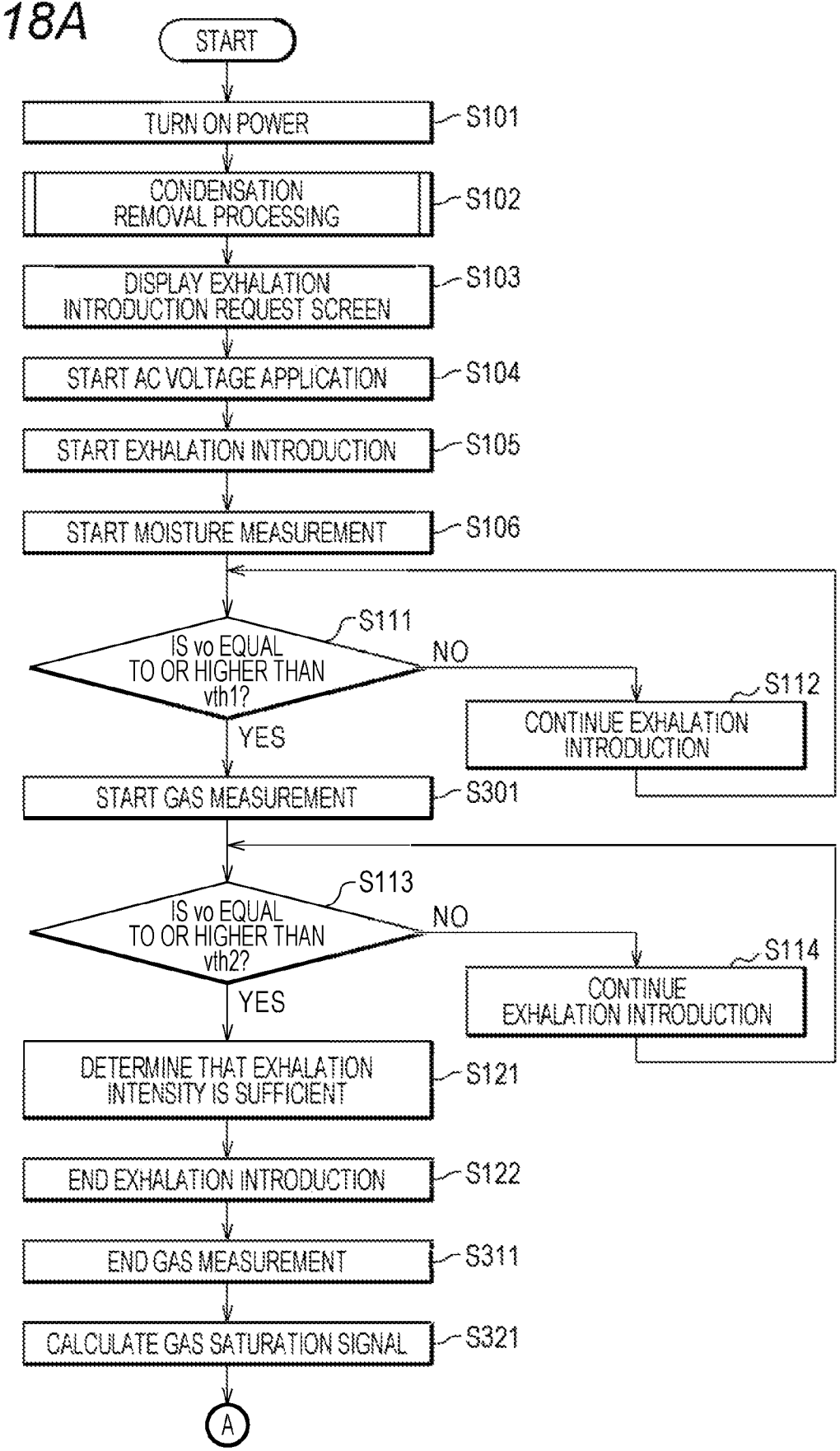
FIG. 18A is a flowchart (part 1) illustrating a procedure of gas detection processing performed in this embodiment.
Figure 18B:
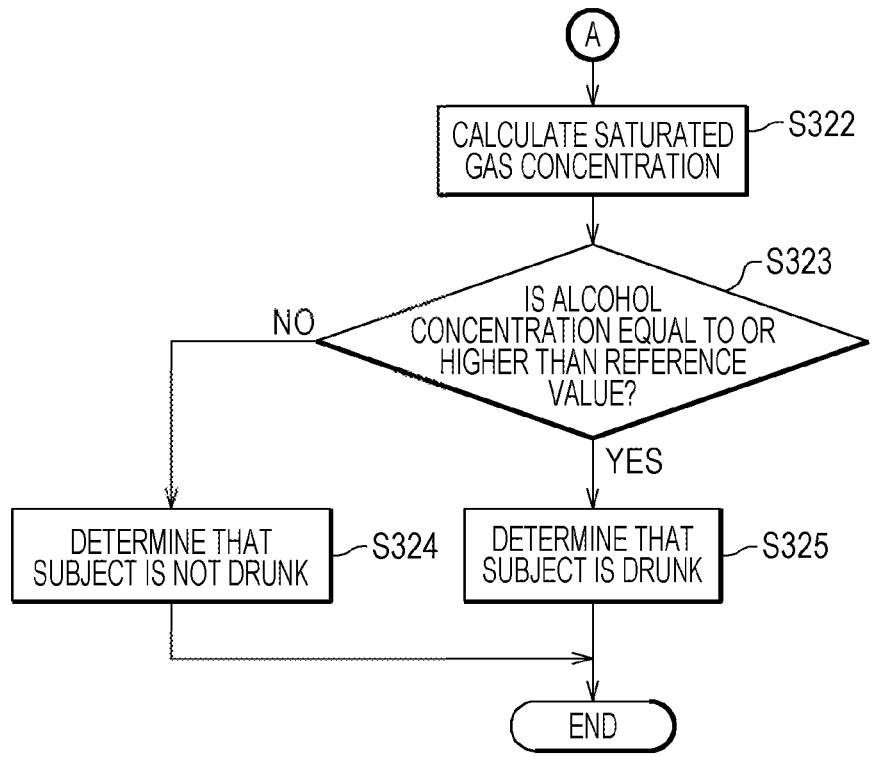
FIG. 18B is a flowchart (part 2) illustrating the procedure of the gas detection processing performed in this embodiment.

FIGS. 18A and 18B are flowcharts illustrating a procedure of the gas detection processing performed in this embodiment. In the processing illustrated in FIGS. 18A and 18B, the processing illustrated in FIG. 15 is used. Incidentally, FIGS. 18A and 18B illustrate a case where the gas to be detected is alcohol, but gases other than alcohol can also be detected by the same procedure. In actual alcohol detection, in addition to alcohol, acetaldehyde, which is a metabolite, and hydrogen, with a high concentration of about 10 ppm in the exhalation, are subject to gas measurement. Then, the alcohol gas concentration is calculated on the basis of the gas concentrations of alcohol, acetaldehyde, and hydrogen. In this way, it is possible to calculate an accurate alcohol gas concentration. Herein, when this method is used, the gas sensor 101c for alcohol, the gas sensor 101d for acetaldehyde, and the gas sensor 101f for hydrogen are used as the gas sensor 101. Hereinafter, each gas sensor 101 of the gas sensor 101c for alcohol, the gas sensor 101d for acetaldehyde, and the gas sensor 101f for hydrogen is referred to as gas sensors 101c, 101d, and 101f, respectively. Further, in the flowcharts of FIGS. 18A and 18B, the same step numbers are assigned to the same processing as those in FIG. 15.

First, steps S101 to S112 in FIG. 18A are the same as the processing of steps S101 to S112 in FIG. 15, and thus the description thereof is omitted here.

As a result of step S111, when the output voltage vo is equal to or higher than the first threshold value vth1 (S111→Yes), the gas measurement processing part 513 starts output measurement (gas measurement) from the gas sensors 101c, 101d, and 101f (S301).

Thereafter, the moisture measurement processing part 512 performs the processing of step S113. The processing in steps S113 to S122 is the same as the processing in steps S113 to S122 in FIG. 15, and thus description thereof is omitted here.

In step S122, the exhalation introduction is completed, and the gas measurement processing part 513 ends the output measurement (gas measurement) from the gas sensors 101c, 101d, and 101f (S311).

Thereafter, the gas measurement processing part 513 calculates the gas saturation signal values of the gas sensors 101c, 101d, and 101f from the output curves from the output start to the output end from the gas sensors 101c, 101d, and 101f (S321). The processing of step S321 will be described later.

Further, the gas measurement processing part 513 calculates each gas concentration (saturated gas concentration) in a saturated state by the differential evolution method on the basis of the calculated gas saturation signal value (S322 in FIG. 18B). Each gas is alcohol, acetaldehyde, hydrogen or the like. In this way, when the saturated gas concentration of a certain gas is calculated using the differential evolution method on the basis of a plurality of saturated gas concentrations, a highly accurate saturated gas concentration can be calculated.

Then, the determination processing part 514 determines whether or not the saturated gas concentration of alcohol (alcohol concentration) among the saturated gas concentrations calculated in step S322 is equal to or higher than a reference value (S323).

As a result of step S323, when the alcohol concentration is less than the reference value (S323→No), the determination processing part 514 determines that the subject is not drunk (S324).

As a result of step S323, when the alcohol concentration is equal to or higher than the reference value (S323→Yes), the determination processing part 514 determines that the subject is drunk (S325).

Figure 19:
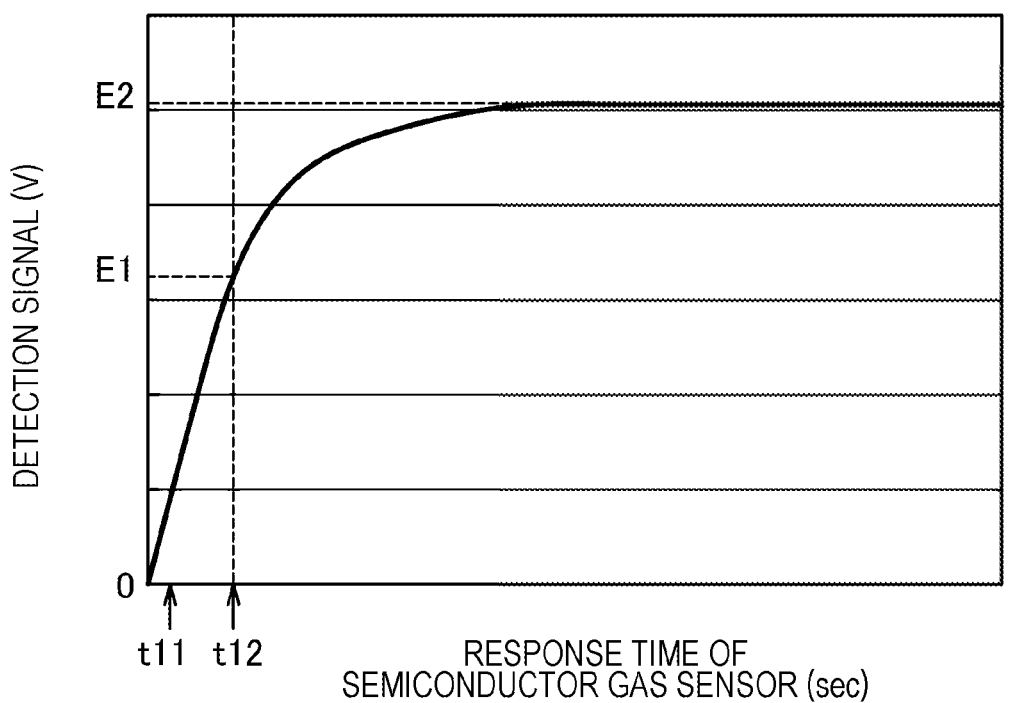
FIG. 19 is a graph illustrating a time change of a detection signal output from a gas sensor 101.

FIG. 19 is a graph illustrating a time change of a detection signal output from the gas sensor 101. In FIG. 19, a vertical axis represents the detection signal (V), and a horizontal axis represents the response time (sec) of the gas sensor 101.

Time t11 in FIG. 19 is time t11 in FIG. 16. That is, FIG. 19 illustrates that the output voltage vo from the moisture detection element 1 exceeds vth1 at time t11. Then, the gas measurement processing part 513 starts gas measurement at time t11 when the output voltage vo from the moisture detection element 1 exceeds vth1 (step S301 in FIG. 18A). Incidentally, since the gas sensor 101 starts to react before the detection of the introduction of exhalation, time t11 is slightly on the + side from the origin.

Time t12 in FIG. 19 is time t12 in FIG. 16. That is, FIG. 19 illustrates that the detection signal reaches the value E1 at time t12, and the output voltage vo from the moisture detection element 1 exceeds vth2. Then, the gas measurement processing part 513 ends the gas measurement at time t12 (S311 in FIG. 18A). Then, the gas measurement processing part 513 estimates a gas saturation signal value E2 on the basis of the value E1 of the detection signal from the gas sensor 101 at time t12. Incidentally, since the gas detection signal rises in a predetermined trend, a gas saturation signal value E2 can be estimated from time t11, time t12, and the detection signal value E1. The time from the start of exhalation introduction to the calculation of the gas saturation signal value E2 is about 3 seconds.

As a method other than the above, the following method may be used. A cover (not illustrated) is often provided around the sensor portion of the gas sensor 101. When the space in the cover becomes small, the space in the cover has the same concentration as the introduced gas even if the amount of gas introduced is small. That is, as the size of the space in the cover in the gas sensor 101 becomes smaller, the time until saturation becomes shorter. Therefore, when the size of the space in the cover in the gas sensor 101 is small, as illustrated in FIG. 19, the gas saturation signal value E2 does not have to be estimated from the detection signal value E1. That is, the gas measurement processing part 513 may directly acquire the gas saturation signal value E2. In the case of such alcohol detection, the gas measurement processing part 513 waits for three to five seconds after the exhalation is introduced. Further, when the detection signal of the gas sensor 101c for alcohol to be measured reaches the peak value, the gas measurement processing part 513 acquires the detection signals of the gas sensor 101d for acetaldehyde and the gas sensor 101f for hydrogen. Then, the gas measurement processing part 513 performs concentration calculation based on the differential evolution method on the basis of the gas saturation signal values acquired directly from the respective gas sensors 101c, 101d, and 101f. Then, the gas measurement processing part 513 calculates an accurate gas saturation concentration of alcohol, acetaldehyde, and hydrogen.

Incidentally, the time from time t11 to time t12 is about one to two seconds. In other words, the gas measurement can be performed with a measurement of about one to two seconds, and time can be greatly reduced.

As described above, according to the exhalation test system Z using the moisture detection element 1 of this embodiment, it is possible to test a gas (for example, alcohol) in a considerably short time. In particular, it is possible to determine whether or not the introduced exhalation is actually exhalation and to determine whether or not the subject is drunk in a short measurement time.

[Exhalation Test Device 700]

Next, an example of an exhalation test device 700 including the exhalation sensor 100 according to this embodiment will be described with reference to FIGS. 20 to 22.

(Mobile Type)

Figure 20:
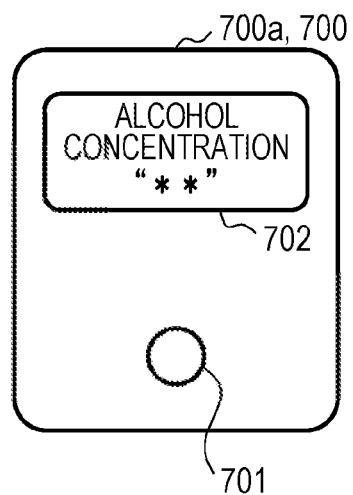

FIG. 20 is a view illustrating an example (first example) of a mobile type exhalation test device 700a (700).

The exhalation test device (portable terminal) 700a illustrated in FIG. 20 has, for example, a business card size.

The exhalation test device 700a includes an exhalation introduction port (exhalation introduction part) 701 and a display screen 702. An exhalation detector 300, an analysis device 500, a transmission device 601, and a storage device 602 illustrated in FIG. 12 are mounted inside the exhalation test device 700a. In addition, the display screen 702 corresponds to the display device 504 in FIG. 14.

In other words, in the exhalation introduced into the exhalation test device 700a from the exhalation introduction port 701, the exhalation and gas are detected by the internal exhalation sensor 100. Then, a test result by the exhalation test device 700a is displayed on the display screen 702.

Incidentally, the exhalation sensor 100 mounted in the exhalation test device 700a may be the exhalation sensor 100a illustrated in FIG. 9 or the exhalation sensor 100b illustrated in FIG. 10.

Figure 21:
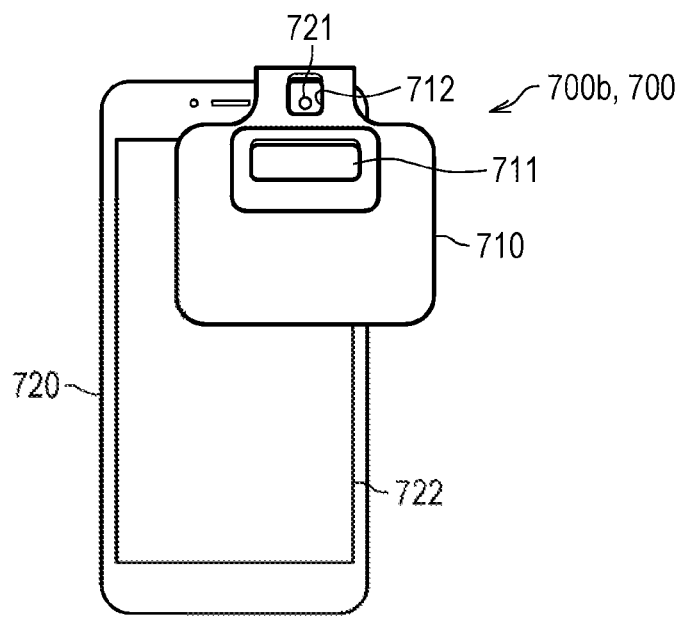
FIG. 21 is a view illustrating an example (Example 2) of a mobile type exhalation test device 700b.

FIG. 21 is a view illustrating an example (second example) of a mobile type exhalation test device 700b.

The exhalation test device (portable terminal) 700b (700) illustrated in FIG. 21 is of a type in which an exhalation introduction device 710 is attached to a smartphone 720.

The exhalation introduction device 710 is connected to the smartphone 720 by, for example, a universal serial bus (USB) or the like.

Incidentally, in the exhalation test device 700b illustrated in FIG. 21, the exhalation detector 300 illustrated in FIG. 12 is mounted in the exhalation introduction device 710. In addition, the analysis device 500, the transmission device 601, and the storage device 602 are mounted on the smartphone 720 in the form of an application.

The exhalation introduction device 710 is provided with an exhalation introduction port (exhalation introduction part) 711.

In other words, in the exhalation introduced into the exhalation introduction device 710 from the exhalation introduction port 711, the exhalation and gas are detected by the internal exhalation sensor 100 (see FIG. 12). Then, the result of the exhalation test performed on the smartphone 720 is displayed on the display screen 722 of the smartphone 720. In addition, the display screen 722 corresponds to the display device 504 in FIG. 14.

Incidentally, as illustrated in FIG. 21, the exhalation introduction device 710 is provided with an opening 712 so as not to block a camera (imaging part) 721 of the smartphone 720 when attached to the smartphone 720. In this way, the camera 721 of the smartphone 720 can be used, and the spoofing prevention processing described later can be performed. Incidentally, the camera 721 corresponds to the imaging device 506 in FIG. 14.

Since the moisture detection element 1 can be downsized, the exhalation test device 700 such as the exhalation test device 700a illustrated in FIG. 20 and the exhalation test device 700b illustrated in FIG. 21 can be downsized. When the exhalation test device 700a is downsized in this way, the exhalation test device can be used for home use or be attached to a bicycle, thereby providing a healthcare product that can be used easily.

FIG. 22 is a view illustrating an example of an exhalation test device 700c which is provided in an automobile 801.

As illustrated in FIG. 22, in the exhalation test device 700c (700), the exhalation introduction device 730 is provided in the automobile 801. Incidentally, in the system illustrated in FIG. 22, the exhalation detector 300 in FIG. 12 is mounted on the exhalation introduction device 730. In addition, the analysis device 500, the transmission device 601, and the storage device 602 are mounted on an engine control unit (ECU) (not illustrated).

The exhalation introduction device 730 includes an exhalation introduction port (not illustrated).

That is, in the exhalation introduced into the exhalation introduction device 730, the exhalation and gas are detected by the internal exhalation sensor 100 (see FIG. 12) or the ECU. Further, when alcohol is detected, the ECU performs an interlock function to prevent starting an engine (not illustrated) or depressing the accelerator pedal, for example.

Second Embodiment (Spoofing Prevention Processing)

Figure 23A:
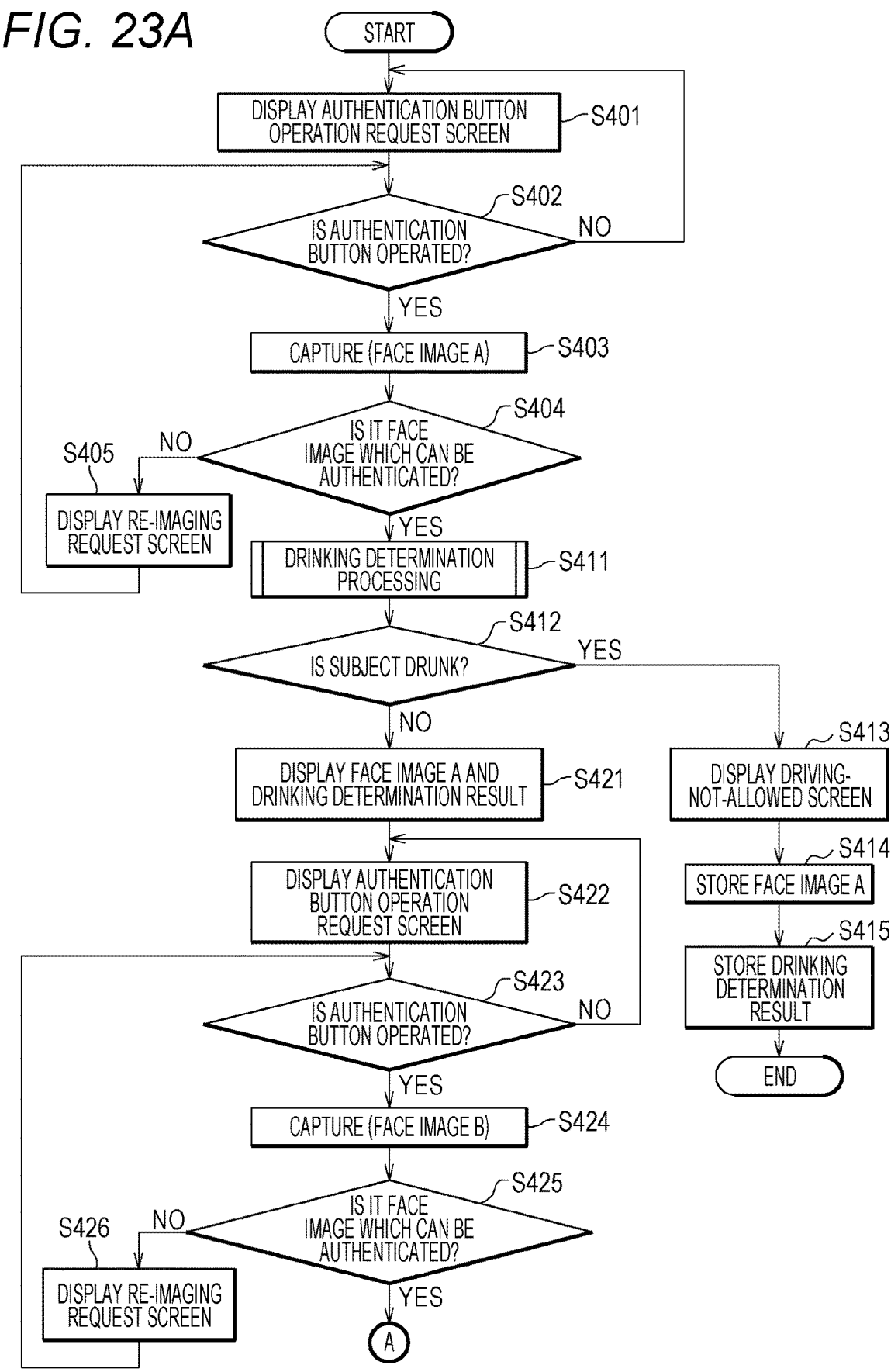
FIG. 23A is a flowchart (part 1) illustrating a procedure of spoofing prevention processing performed in this embodiment.
Figure 23B:
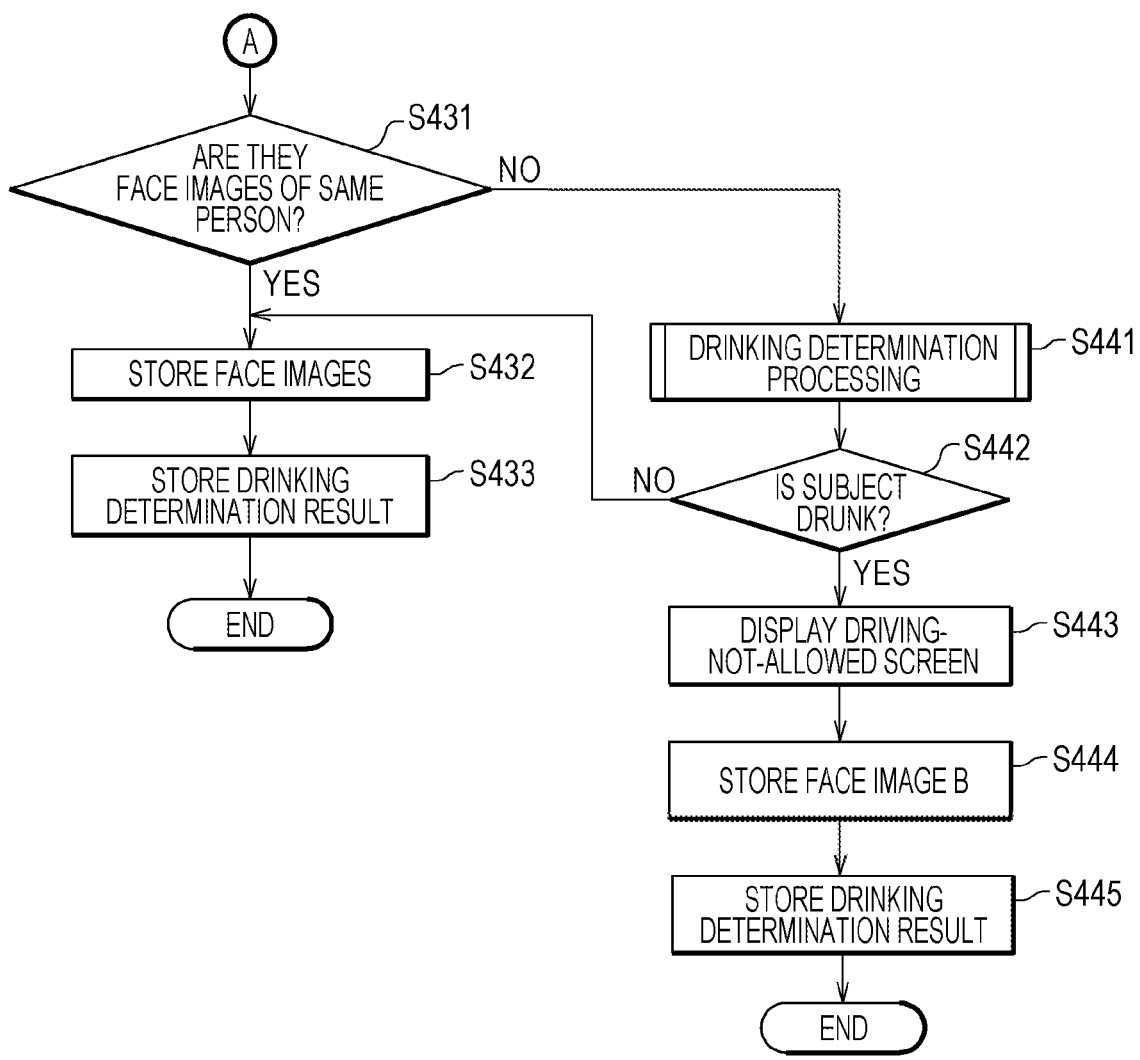
FIG. 23B is a flowchart (part 2) illustrating the procedure of the spoofing prevention processing performed in this embodiment.

FIG. 23A and FIG. 23B are flowcharts showing a procedure of spoofing prevention processing performed in this embodiment. FIG. 23A and FIG. 23B are the processing performed in the exhalation test system Z that can use the camera 721 as illustrated in FIG. 21, for example. In addition, FIG. 23A and FIG. 23B are the processing performed before driving the automobile 801 (see FIG. 22).

In FIGS. 23A and 23B, FIG. 14 is referred to as appropriate.

First, after the exhalation test system Z is turned on, the authentication processing part 515 of the analysis device 500 displays information (authentication button operation request screen) that prompts the user to operate the authentication button on the display device 504 (S401).

Next, the authentication processing part 515 determines whether or not the authentication button is operated (S402). In the example of FIG. 21, the authentication button is a button displayed on the display screen 722 of the smartphone 720, and is operated by the user. In the example of FIG. 22, the authentication button is a button displayed on a car navigation screen (not illustrated). In addition, when the mobile type exhalation test device 700b as illustrated in FIG. 21 is applied to the type provided in the automobile 801 as illustrated in FIG. 22, the following configuration is required. That is, the smartphone 720 and the analysis device 500 provided in the vehicle can communicate with each other by proximity communication or the like. Then, a detection signal of the moisture detection element 1, the gas sensor 101, and the like, a face image captured by the camera 721 as necessary, and the like are transmitted from the smartphone 720 to the analysis device 500 provided in the vehicle.

As a result of step S402, when the authentication button is not operated (S402→No), the authentication processing part 515 returns the process to step S401.

As a result of step S402, when the authentication button is operated (S402→Yes), the imaging device 506 captures a face image (S403). The face image captured at this time is referred to as a face image A.

Thereafter, the authentication processing part 515 determines whether or not the captured face image A is a face image which can be authenticated (S404). The face image which can be authenticated is a face image that can be used for determining whether or not the subject is the same person as compared to a face image B that is captured later. Specifically, eyes, nose, mouth, outline, and the like are reflected.

As a result of step S404, when the face image is not the face image which can be authenticated (S404→No), the authentication processing part 515 displays information (re-imaging request screen) prompting re-imaging on the display device 504 (S405) and returns the process to step S402.

As a result of step S404, when the face image is the face image which can be authenticated (S404→Yes), the exhalation test system Z performs drinking determination processing by performing the processing starting from step S102 in FIG. 18A (S411).

Next, the authentication processing part 515 determines whether or not the subject is drunk using the result of the drinking determination processing in step S411 (S412).

As a result of step S412, when the subject is drunk (S412→Yes), the authentication processing part 515 displays information (driving-not-allowed screen) indicating that driving is not allowed on the display device 504 (S413). Incidentally, when the exhalation test system Z is a system as illustrated in FIG. 22, the exhalation test system Z may perform an interlock when the determination of "Yes" is made in step S412.

After that, the authentication processing part 515 stores the face image A (S414) and stores the result of step S411 (drinking determination result) in the storage device 505 (S415).

As a result of step S412, when the subject is not drunk (S412→No), the authentication processing part 515 displays the face image A and the result of drinking determination processing (drinking determination result) on the display device 504 (S421).

Then, the authentication processing part 515 displays information (authentication button operation request screen) that prompts the user to operate an authentication button (not illustrated) on the display device 504 (S422). The authentication button is the same as that displayed in step S402.

Next, the authentication processing part 515 determines whether or not the authentication button is operated (S423).

As a result of step S423, when the authentication button is not operated (S423→No), the authentication processing part 515 returns the process to step S422.

As a result of step S423, when the authentication button is operated (S423→Yes), the imaging device 506 captures a face image (S424). The face image captured at this time is referred to as a face image B.

Thereafter, the authentication processing part 515 determines whether or not the captured face image B is the face image which can be authenticated (S425). The face image which can be authenticated is the same as that in step S404, and thus, the description thereof is omitted here.

As a result of step S425, when the face image is not the face image which can be authenticated (S425→No), the authentication processing part 515 displays information (re-imaging request screen) prompting re-imaging on the display device 504 (S426). Thereafter, the authentication processing part 515 returns the process to step S423.

As a result of step S425, when the face image is the face image which can be authenticated (S425→Yes), the authentication processing part 515 compares the face image A with the face image B. Accordingly, the authentication processing part 515 determines whether or not the face image A and the face image B are face images of the same person (S431 in FIG. 23B).

As a result of step S431, when face image A and face image B are face images of the same person (S431→Yes), the authentication processing part 515 stores the face image A and the face image B in the storage device 505 (S432). Thereafter, the authentication processing part 515 stores the result (drinking determination result) of the drinking determination processing in step S411 in association with the face images A and B in the storage device 505 (S433) and ends the processing.

As a result of step S431, when the face image A and face image B are not the face image of the same person (S431→No), the exhalation test system Z performs the drinking determination processing again by performing the processing starting from step S102 of FIG. 18A (S441).

Next, the authentication processing part 515 determines whether or not the subject is drunk using the result of the drinking determination processing in step S441 (S442).

As a result of step S442, when the subject is not drunk (S442→No), the authentication processing part 515 stores the face image B in the storage device 505 (S432).

Thereafter, authentication processing part 515 stores the result (drinking determination result) of drinking determination processing in step S422 in association with the face image B in storage device 505 (S433) and ends the processing.

As a the result of step S442, when the subject is drunk (S442→Yes), the authentication processing part 515 displays information indicating that driving is not allowed (driving-not-allowed screen) on the display device 504 (S443). Incidentally, when the exhalation test system Z is a system as illustrated in FIG. 22, the exhalation test system Z may perform an interlock when the determination of "Yes" is made in step S442.

After that, the authentication processing part 515 stores the face image B (S444) and stores the result of step S441 (drinking determination result) in association with the face image B in the storage device 505 (S445).

For example, the authentication button depression in step S402 may be performed immediately before leaving the office or the like, and the authentication button depression in step S423 may be performed immediately before the accelerator pedal is depressed.

Incidentally, in the case of the automobile 801 (see FIG. 22) driven by a professional driver such as a taxi driver, the authentication processing part 515 may store the face image and the drinking determination result in association with the tachometer information. Even in the case of a general driver, the face image and the drinking determination result may be stored as evidence of the drinking test.

By such a spoofing prevention processing, the face image A before the exhalation introduction and the face image B after the exhalation introduction are compared to prevent drunk driving using spoofing. For example, the face image A is a face image captured before boarding, and the face image B is a face image captured after boarding.

Third Embodiment (High-Temperature Type and Low-Temperature Type)

Figure 24A:
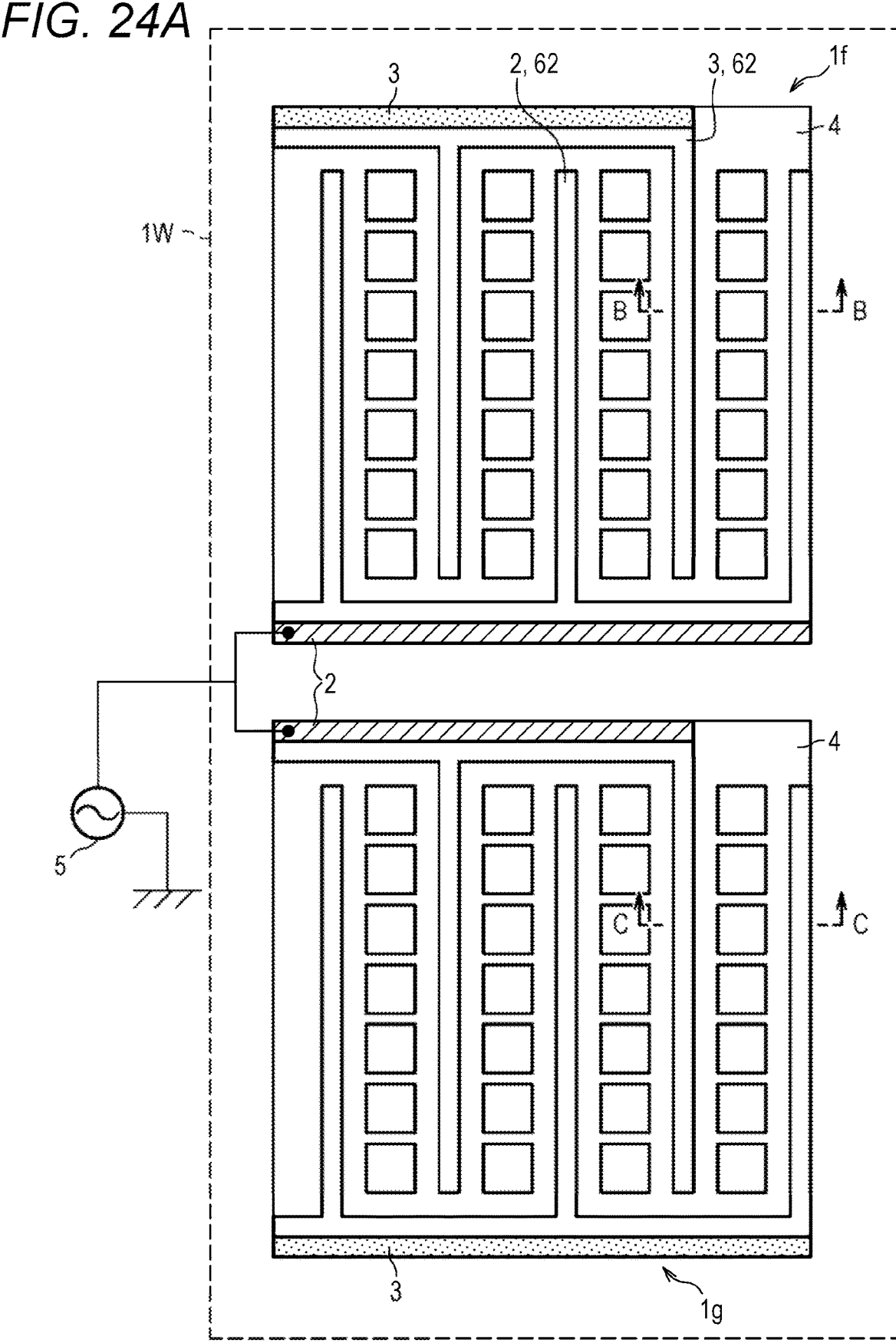
FIG. 24A is a view illustrating an example of a top view of a moisture detection element 1W having a low-temperature type and a high-temperature type.
Figure 24B:
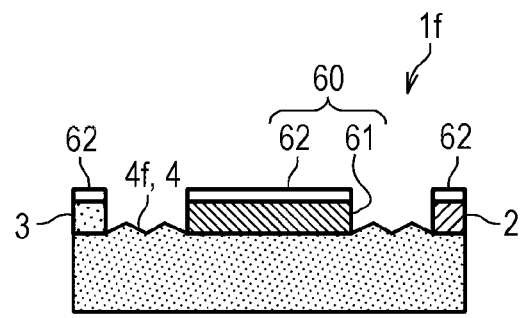
FIG. 24B is a schematic cross-sectional view of a low-temperature type moisture detection element 1f.
Figure 24C:
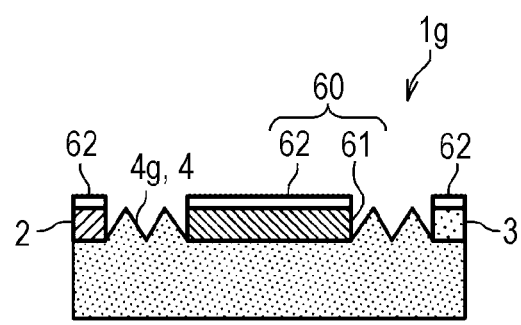
FIG. 24C is a schematic cross-sectional view of a high-temperature type moisture detection element 1g.

FIGS. 24A to 24C are views illustrating an example of a moisture detection element 1W having a low-temperature type and a high-temperature type. FIG. 24A illustrates a top view of the moisture detection element 1W. FIG. 24B is a schematic cross-sectional view taken along line B-B in FIG. 24A, and FIG. 24C is a schematic cross-sectional view taken along line C-C in FIG. 24A.

The unevenness structure of the insulating substrate 4 can be distinguished into a low-temperature type used in a low-temperature environment (under an environment below a predetermined temperature) illustrated in FIG. 24B and a high-temperature type used in a high-temperature environment (under an environment above a predetermined temperature) illustrated in FIG. 24C.

That is, as illustrated in FIG. 24B, the low-temperature type moisture detection element 1f has a smaller unevenness on the insulating substrate 4f (4) than the high-temperature type moisture detection element 1g illustrated in FIG. 24C. On the contrary, in the high-temperature type, as illustrated in FIG. 24C, the unevenness of the insulating substrate 4g (4) is made larger than in the low-temperature type illustrated in FIG. 24B. Incidentally, the low-temperature type moisture detection element 1f and the high-temperature type moisture detection element 1g are the same as the moisture detection element 1 illustrated in FIGS. 1 to 2B except for the shape of the insulating substrate 4. Thus, the elements other than the insulating substrate 4 are denoted by the same reference numerals, and the description is omitted.

Since the amount of saturated water vapor increases at a high temperature, the exhalation humidity (relative humidity) decreases. For this reason, in the high-temperature type, as illustrated in FIG. 24C, the unevenness of the insulating substrate 4g is increased so that moisture (water molecules 11 (see FIG. 2A)) is easily attached. In this way, it is possible to provide the moisture detection element 1g that operates properly even in a high-temperature environment where the exhalation humidity is low.

On the contrary, since the amount of saturated water vapor decreases at low temperatures, the exhalation humidity (relative humidity) increases. In such a state, when the unevenness of the insulating substrate 4 is increased, moisture (water molecules 11) adheres excessively. For this reason, in the low-temperature type moisture detection element 1f, as illustrated in FIG. 24B, by reducing the unevenness of the insulating substrate 4f, moisture (water molecules 11) is less likely to adhere compared to the high-temperature type moisture detection element 1g. In this way, it is possible to provide the moisture detection element 1f that operates properly even in a low temperature environment where the exhalation humidity becomes high.

Further, as illustrated in FIG. 24A, the AC voltage vi is applied from the power supply 5 to the low-temperature type moisture detection element 1f and the high-temperature type moisture detection element 1g. By adopting such a configuration, it is possible to provide the moisture detection element 1W that can be used in either a low-temperature environment or a high temperature environment.

Incidentally, in the example of FIGS. 24A to 24C, the size of the unevenness of the insulating substrate 4 is two types of a low-temperature type and a high-temperature type, but may be three or more types. That is, the moisture detection element 1W having the insulating substrate 4 suitable for the intermediate temperature between the low-temperature type and the high-temperature type may be provided by increasing the unevenness as the low-temperature type changes to the high-temperature type. Incidentally, the low-temperature type moisture detection element if and the high-temperature type moisture detection element 1g may be switched in accordance with the ambient temperature.

Here, the unevenness of the insulating substrate 4 may have a mountain shape as illustrated in FIGS. 24B and 24C. However, the invention is not limited thereto, and the unevenness may have, for example, a protrusion shape. Alternatively, the unevenness of the insulating substrate 4 may be formed in a shape such as a random shape other than a mountain shape or a protrusion shape.

Incidentally, the size of the unevenness of the insulating substrate 4 is the difference between the height and depth of the unevenness and the size of the undulations. Here, the height of the unevenness of the insulating substrate 4 is nano level, for example, about 1 nm to 100 nm.

Although the conductive film 61 is assumed to be a metal, the conductive film 61 is not limited to a metal as long as it has conductivity. For example, graphite or the like may be used as the conductive film 61.

Modification

FIGS. 25 to 28B illustrate a modification of the moisture detection element 1 according to this embodiment. In FIGS. 25 to 28B, the same components as those in FIGS. 1 and 2A are denoted by the same reference numerals as those in FIGS. 1 and 2A.

Figure 25:
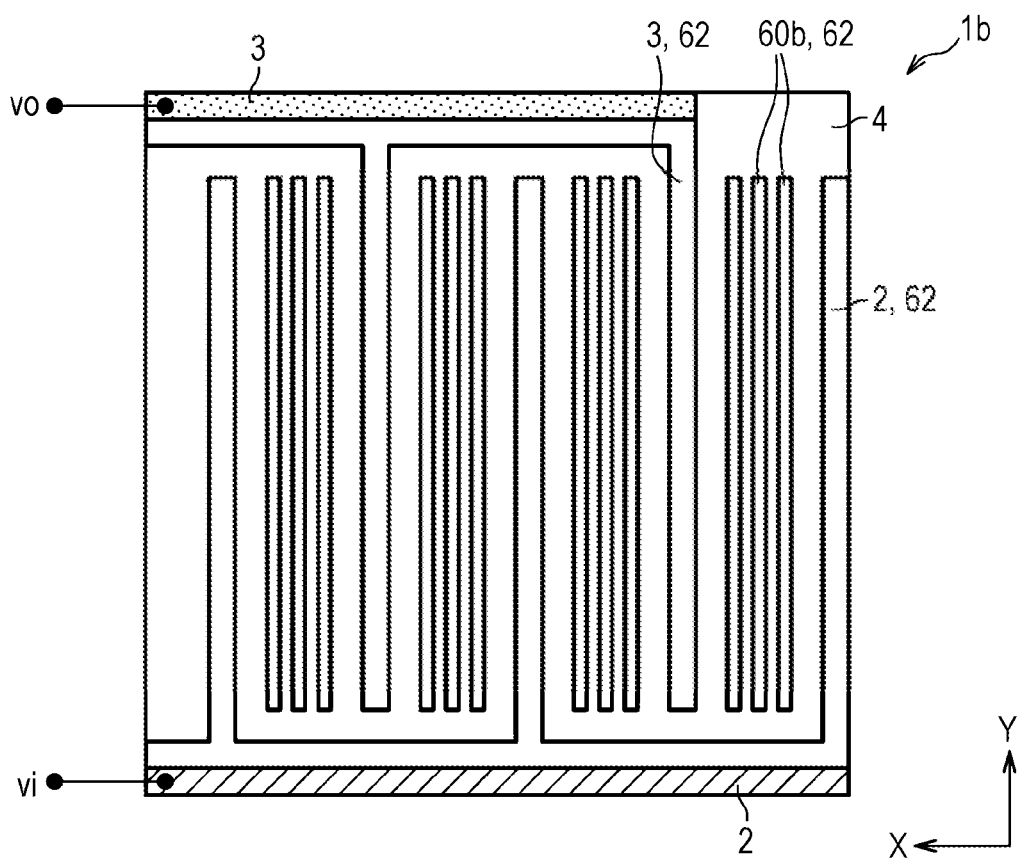
FIG. 25 is a view illustrating a first modification of the moisture detection element according to this embodiment.

FIG. 25 is a view illustrating a first modification of the moisture detection element 1 according to this embodiment.

A moisture detection element 1b illustrated in FIG. 25 includes an auxiliary electrode 60b divided between the application electrode 2 and the detection electrode 3 in a strip shape in the vertical direction (Y direction).

FIG. 26 is a view illustrating a second modification of the moisture detection element 1 according to this embodiment.

A moisture detection element 1c illustrated in FIG. 26 includes one auxiliary electrode 60c between the application electrode 2 and the detection electrode 3.

Figure 27:
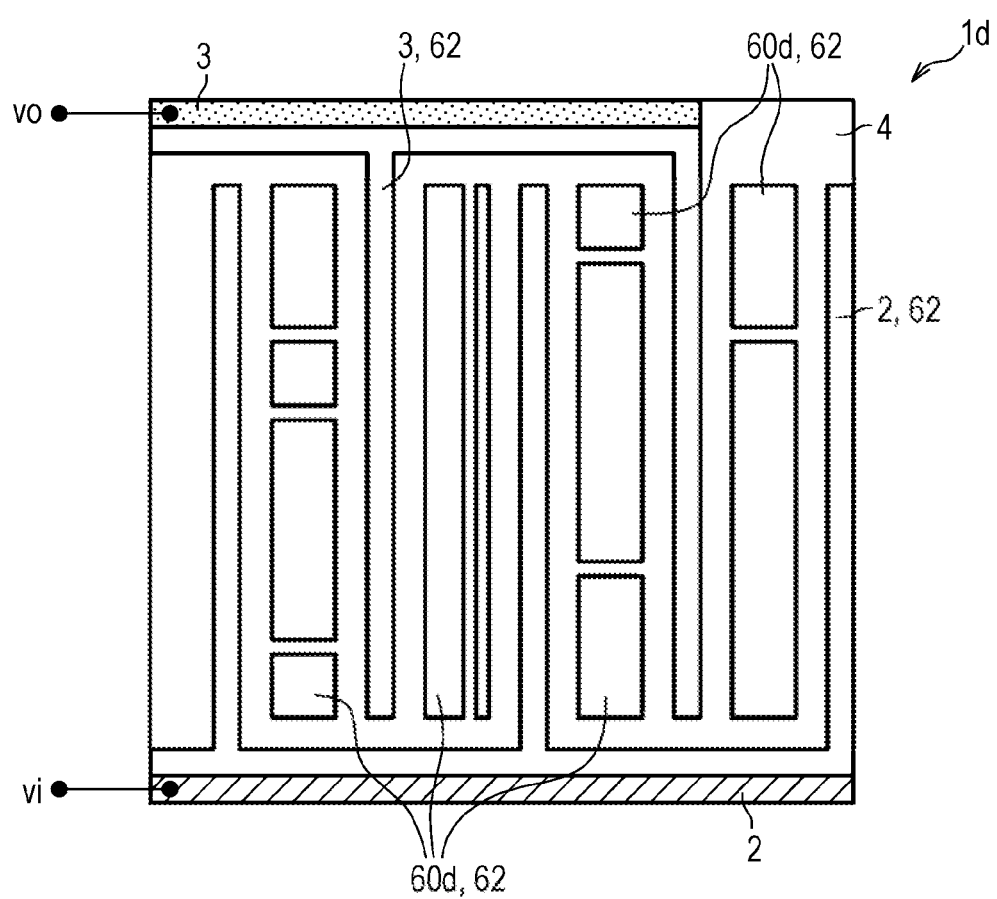
FIG. 27 is a view illustrating a third modification of the moisture detection element according to this embodiment.

FIG. 27 is a view illustrating a third modification of the moisture detection element 1 according to this embodiment.

In a moisture detection element 1d illustrated in FIG. 27, the shape of the auxiliary electrode 60d does not have the same shape between the application electrode 2 and the detection electrode 3.

Figure 28A:
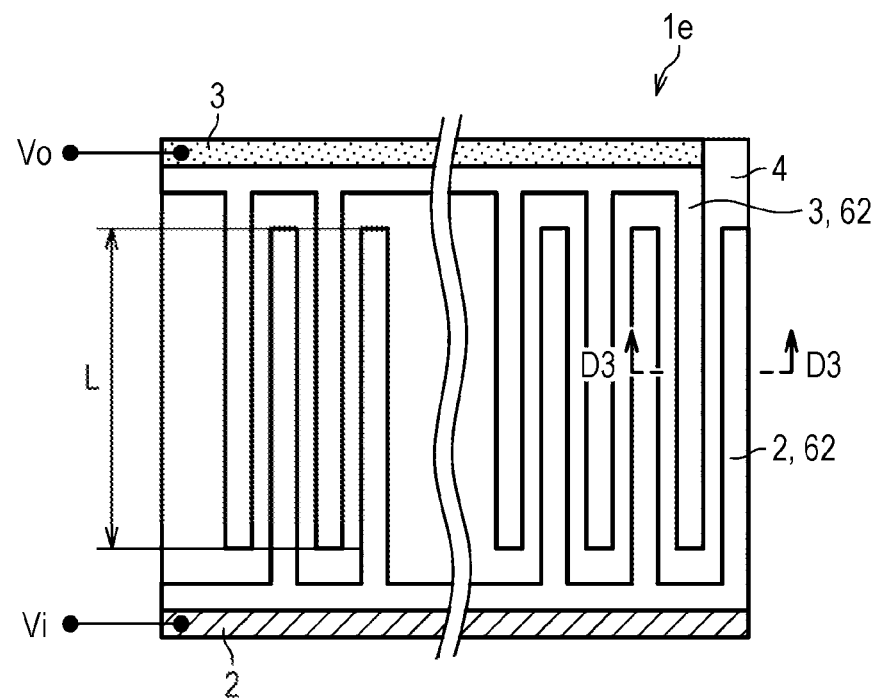
FIG. 28A is a view (part 1) illustrating a fourth modification of the moisture detection element in this embodiment.
Figure 28B:
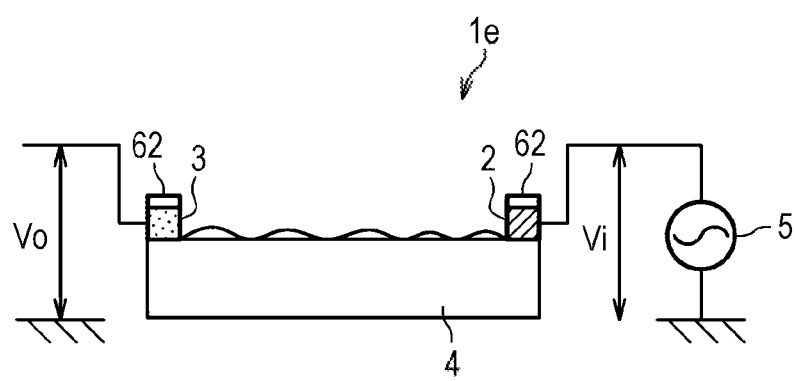
FIG. 28B is a view (part 2) illustrating the fourth modification of the moisture detection element according to this embodiment.

FIGS. 28A and 28B are views illustrating a fourth modification of the moisture detection element 1 in this embodiment.

In a moisture detection element 1e illustrated in FIGS. 28A and 28B, the auxiliary electrode 60 of the moisture detection element 1 in FIG. 1 is omitted. Thus, although the auxiliary electrode 60 is omitted, if the insulating film 62 is formed on the application electrode 2 and the detection electrode 3, the occurrence of errors due to the dust 12 can be reduced.

Incidentally, the present invention is not limited to the above-described embodiments, and various modifications are included. For example, the above-described embodiments have been described in detail for easy understanding of the invention and are not necessarily limited to those having all the described configurations. In addition, a part of the configuration of a certain embodiment can be replaced with the configuration of another embodiment, and the configuration of another embodiment can be added to the configuration of a certain embodiment. Further, it is possible to add, delete, and replace other configurations for a part of the configuration of each embodiment.

Each of the above-described configurations, functions, parts 411 and 511 to 515, storage devices 505 and 602, or the like may be realized by hardware by designing a part or all of them, for example, with an integrated circuit. Further, as illustrated in FIG. 14, the above-described configurations, functions, and the like may be realized by software by a processor such as the CPU 502 interpreting and executing a program that realizes each function. Information such as programs, tables, and files that realize each function can be stored in a recording devices such as a hard disk (HD), the memory 501, and a solid state drive (SSD) or a recording medium such as an integrated circuit (IC) card, a secure digital (SD) card, or a digital versatile disc (DVD).

Further, in each embodiment, control lines and information lines are those that are considered necessary for explanation, and not all control lines and information lines are necessarily shown on the product. In practice, it may be considered that almost all configurations are connected to each other.

It is understood that the foregoing description is that of the preferred embodiments of the invention and that various changes and modifications may be made thereto without departing from the spirit and scope of the invention as defined in the appended claims.

What is claimed is:

1. A moisture detection element comprising:
   an insulating substrate of an insulating material;
   an application part which is formed on the insulating substrate and to which a voltage is applied; and
   an output part which is formed on the insulating substrate and configured to output a voltage signal in response to a current flowing through an electric path via water molecules adhering to a surface area of the insulating substrate under the voltage applied to the application part,
   an intermediate part which is formed on the insulating substrate intermediate between the application part and the output part to reduce the surface area to which the water molecules adhere, and arranged to be in the electric path such that the current flowing through the electric path via the water molecules, also flows through the intermediate part;
   wherein
   an insulation of an insulating material is provided on the application part and the output part.

2. The moisture detection element according to claim 1, wherein the intermediate part comprises:
a conductive part which is electrically insulated from the application part and the output part and is provided on the insulating substrate, wherein
the insulation is provided on the conductive part.

3. The moisture detection element according to claim 2, wherein
plural conductive parts and plural insulations are arranged in a divided manner between the application part and the output part.

4. The moisture detection element according to claim 1, wherein
a heater is provided on the insulating substrate.

5. The moisture detection element according to claim 1, wherein
in the application part and the output part, the insulation is provided in a range where a short circuit is likely to occur due to adhesion of dust.

6. The moisture detection element according to claim 1, wherein
the insulation includes an organic film or a metal oxide film.

7. The moisture detection element according to claim 1, wherein
the voltage applied to the application part is an AC voltage.

8. The moisture detection element according to claim 1, wherein
the insulating substrate has a structure in which oxygen atoms are arranged on at least a surface of the insulating substrate.

9. The moisture detection element according to claim 1, wherein
the insulating substrate has unevenness provided on the surface to which the water molecules adhere.

10. An exhaled gas detector comprising:
a moisture detection part which includes: an insulating substrate of an insulating material; an application part which is formed on the insulating substrate and to which a voltage is applied; an output part which is formed on the insulating substrate and configured to output a voltage signal in response to a current flowing through an electric path via water molecules adhering to a surface area of the insulating substrate under the voltage applied to the application part; an intermediate part which is formed on the insulating substrate intermediate between the application part and the output part to reduce the surface area to which the water molecules adhere, and arranged to be in the electric path such that the current flowing through the electric path via the water molecules, also flows through the intermediate part;
and in which an insulation of an insulating material is provided on the application part and the output part;
a gas detection part configured to measure a concentration of gas contained in an outside air;
an analysis part configured to analyze the voltage signal output from the moisture detection part and a detection signal output from the gas detection part; and
a display part configured to display a result analyzed by the analysis part, wherein
the analysis part determines that the introduced outside air is a human exhalation on a basis of the voltage signal output from the moisture detection part and then calculates a concentration of gas contained in the outside air introduced from the gas detection part.

11. The exhaled gas detector according to claim 10, wherein the intermediate part comprises:
a conductive part which is electrically insulated from the application part and the output part and is provided on the insulating substrate, wherein
the insulation is provided on the conductive part.

12. The exhaled gas detector according to claim 10, wherein
the gas detection part includes at least one of ethanol, acetaldehyde, and hydrogen gas sensors.

13. An exhalation test system comprising:
a moisture detection part which includes: an insulating substrate of an insulating material an application part which is formed on the insulating substrate and to which a voltage is applied; an output part which is formed on the insulating substrate and configured to output a voltage signal in response to a current flowing through an electric path via water molecules adhering to a surface area of the insulating substrate under the voltage applied to the application part; an intermediate part which is formed on the insulating substrate intermediate between the application part and the output part to reduce the surface area to which the water molecules adhere, and arranged to be in the electric path such that the current flowing through the electric path via the water molecules, also flows through the intermediate part;
and in which an insulation of an insulating material is provided on the application part and the output part;
an exhalation introduction part into which exhalation is introduced; and
a gas measurement part which is installed around the moisture detection part and configured to measure a concentration of a predetermined type of gas.

14. The exhalation test system according to claim 13, wherein the intermediate part comprises:
a conductive part which is electrically insulated from the application part and the output part and is provided on the insulating substrate, wherein
the insulation is provided on the conductive part.

15. The exhalation test system according to claim 13, wherein
the moisture detection part, the gas measurement part, and the exhalation introduction part are installed in a portable terminal.

16. The moisture detection element according to claim 4, wherein
the insulating substrate has a structure in which oxygen atoms are arranged on at least a surface of the insulating substrate.

* * * * *